US007425579B2

(12) United States Patent
Poulin et al.

(10) Patent No.: US 7,425,579 B2
(45) Date of Patent: Sep. 16, 2008

(54) METHODS FOR INHIBITING ACTIVITY OF POLYAMINE TRANSPORTERS

(75) Inventors: Richard Poulin, Sainte-Foy (CA); Marie Audette, Cap-Rouge (CA); René Charest-Gaudreault, St-Nicolas (CA)

(73) Assignee: Universite Laval, Quebec (CA)

( * ) Notice: Subject to any disclaimer, the term of this patent is extended or adjusted under 35 U.S.C. 154(b) by 370 days.

(21) Appl. No.: 11/128,199

(22) Filed: May 13, 2005

(65) Prior Publication Data

US 2005/0267220 A1    Dec. 1, 2005

Related U.S. Application Data

(63) Continuation-in-part of application No. 09/529,319, filed as application No. PCT/US98/07806 on Apr. 21, 1998, now Pat. No. 6,949,679.

(51) Int. Cl.
    $A61K\ 31/165$    (2006.01)
(52) U.S. Cl. ........................ 514/617; 514/646
(58) Field of Classification Search ................ 514/617, 514/646
    See application file for complete search history.

(56) References Cited

U.S. PATENT DOCUMENTS

| | | | |
|---|---|---|---|
| 3,200,106 A | 8/1965 | Dickson et al. | |
| 3,201,472 A | 8/1965 | Spivack | |
| 4,631,337 A | 12/1986 | Tomalia et al. | |
| 4,720,489 A | 1/1988 | Shander | |
| 4,990,672 A | 2/1991 | Johnson et al. | |
| 5,456,908 A | 10/1995 | Aziz et al. | |
| 5,648,394 A | 7/1997 | Boxall et al. | |
| 6,031,003 A * | 2/2000 | Nemeth et al. | 514/579 |
| 6,083,496 A | 7/2000 | Poulin et al. | |
| 6,656,498 B1 * | 12/2003 | Gao | 424/450 |
| 6,673,192 B1 | 1/2004 | Woods et al. | |

FOREIGN PATENT DOCUMENTS

| | | |
|---|---|---|
| WO | WO 93/04373 B1 | 3/1993 |
| WO | WO 93/12777 B1 | 7/1993 |
| WO | WO 98/17623 B2 | 4/1998 |

OTHER PUBLICATIONS

Ajani, et al., "Alterations in Polyamine Metabolism during Continuous Intravenuous Infusion of α-Difluoromethylornithine Showing Correlation of Thrombocytopenia with α-Difluoromethylornithine Plasma Levels," Cancer Research, Oct. 15, 1989, pp. 5761-5765, 49, American Association for Cancer Research, Baltimore, MD, USA.
Antony, et al., "Cellular Polyamines Promote the Aggregation of α-Synuclein," The Journal of Biological Chemistry, Jan. 31, 2003, pp. 3235-3240, vol. 278, No. 5, The American Society for Biochemistry and Molecular Biology, Inc., USA.
Bacchi, C.J., et al., "Parasitic Protozoa and Polyamines," In: Inhibition of Polyamine Metabolism. Biological Significance and Basis for New Therapies, edited by P.P. McCann, A.E. Pegg and A. Sjoerdsma, 1987, pp. 317-344, Academic Press, Orlando, FL, USA.
Bacchi, C.J., et al., "Effects of the Ornithine Decarboxylase Inhibitors DL-α-difluoromethylornithine and α-monofluoromethyldehydroornithine Methyl Ester Alone and in Combination with Suramin Against *Trypanosoma brucei brucei* Central Nervous System Models," Am. J. Trop. Med. Hyg. 1987, pp. 46-52, vol. 36, No. 1, The American Society of Tropical Medicine and Hygiene, USA.
Bacchi, et al., "Polyamine Metabolism as Chemotherapeutic Target in Protozoan Parasites," Mini Reviews in Medicinal Chemistry, 2002, pp. 553-563, vol. 2., No. 6, Bentham Science Publishers, Ltd., USA and NL.
Balfour, et al., "Topical Eflornithine," Am. J. Clin. Dermatol., 2001, pp. 197-201, vol. 2, No. 3, Adis International Limited, Langhorne, PA, USA.
Bandyopadhyay, et al., "Antitumor Activity of a Recombinant Soluble Betaglycan in Human Breast Cancer Xenograft," Cancer Res., Aug. 15, 2002, pp. 4690-4695, 62, American Association for Cancer Research, Baltimore, MD, USA.
Bardocz, S., "The Role of Basolateral Polyamine Uptake in Intestinal Adaptation," In: Polyamines in the Gastrointestinal Tract, edited by R.H. Dowling, U.R. Fölsch and C. Löser., 1992, pp. 409-416, Dordrecht: Kluwer Academic Publ., USA and NL.

(Continued)

Primary Examiner—Shailendra Kumar
(74) Attorney, Agent, or Firm—Buchanan Ingersoll & Rooney, PC

(57) ABSTRACT

A method for inhibiting the activity of a natural polyamine transporter comprising the step of contacting the transporter with an inhibitorily effective amount of a compound of formula (I) or (II):

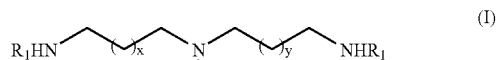

(I)

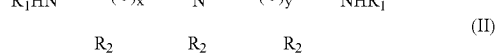

(II)

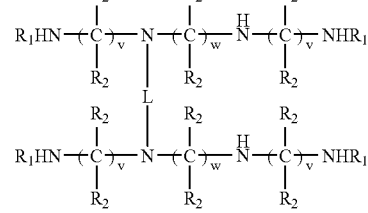

wherein L is a linker; $R_1$=H, methyl, ethyl or propyl; $R_2$=H or methyl; $0<x<3$; $0<y<3$; $2<v<5$; and $2<w<8$. Such a method is particularly useful for treating disorders involving the control of polyamine transport.

29 Claims, 14 Drawing Sheets

OTHER PUBLICATIONS

Bardocz, S., et al., "Effect of Fasting and Refeeding on Basolateral Polyamine Uptake and Metabolism by the Rat Jejunum," In: *Polyamines in the Gastrointestinal Tract*, edited by R.H. Dowling, U.R. Fölsch and C. Löser, 1992, pp. 435-445, Dordrecht: Kluwer Academic Publ., USA and NL.

Bergeron, Raymond J., et al., "Amines and Polyamines from Nitriles," *Synthesis*, 1984, pp. 782-784, Georg Thieme Verlag KG, DE & NY.

Bergeron, Raymond J., et al,. "Reagents for the Stepwise Functionalization of Spermidine, Homospermidine, and Bis(3-aminopropyl)amine," *J. Org. Chem.*, 1984, pp. 2997-3001, vol. 49, No. 16, American Chemical Society, USA.

Bergeron, Raymond J., "Hexahydropyrimidines as Masked Spermidine Vectors in Drug Delivery," *Bioorganic Chem.*, 1986, pp. 345-355,14, Academic Press, Inc./Elsevier Ltd., UK.

Bianchi, et al., "Regulation by Spermine of Native Inward Rectifier $K^+$ Channels in RBL-1 Cells," *J. Biol. Chem.*, Mar. 15, 1996, pp. 6114-6121, vol. 271, No. 11, The American Society for Biochemistry and Molecular Biology, Inc., USA.

Brezinzska, Ewa, et al., "Disulfides. 1. Syntheses Using 2,2'-Dithiobis(benzothiazole)," *J. Org. Chem.*, 1994, pp. 8239-8244, vol. 59, No. 26, American Chemical Society, USA.

Burns, John A., et al.,"Selective Reduction of Disulfides by Tris(2-carboxyethyl)phosphine," *J. Org. Chem.*, 1991, pp. 2648-2650, vol. 56, No. 8, American Chemical Society, USA.

Byers, Timothy L., "Regulation of Polyamine Transport in Chinese Hamster Ovary Cells," *J. Cell. Physiol.*, 1990, pp. 460-467, vol. 143, Journal of Cellular Physiology, Wiley-Liss, Inc., USA.

Carrillo, et al., "Sensitivity of Trypanosomatid Protozoa to DFMO and Metabolic Turnover of Ornithine Decarboxylase," *Biochem Biophys Res. Commun.*, 2000, pp. 663-668, vol. 279, No. 2, Academic Press, UK.

Coffino, Philip, "Regulation of Cellular Polyamines by Antizyme," *Nat. Rev. Mol. Cell Biol.*, Mar. 2001, pp. 188-194, vol. 2, No. 3, Macmillan Magazines Ltd., UK.

Covassin, et al., "Synthesis of Spermidine and Norspermidine Dimers as High Affinity Polyamine Transport Inhibitors," *Bioorg. Med. Chem. Lett.*, 1999, pp. 1709-1714, Elsevier Science Ltd./Pergamon Press, London, England.

Das, et al., "Combined Action of Inhibitors of Polyamine Biosynthetic Pathway with a Known Antimalarial Drug Chloroquine on *Plasmodium falciparum*," *Pharmacol. Res. The Journal of the Italian Pharmacological Society*, 1995, pp. 189-193, vol. 31, No. 3/4, Academic Press, London, England; San Diego, CA, USA.

Gerner, et al., "Polyamines and Cancer : Old Molecules, New Understanding," *Nat. Rev. Cancer*,. Oct. 2004, pp. 781-792, vol. 4, London, England.

Gomes-Trolin, et al., "Increased Red Blood Cells Polyamines in ALS and Parkinson's Disease," *Exp. Neurol.* 2002, pp. 515-520, vol. 177, Academic Press/Elsevier Science, Orlando, FL.

Gordonsmith, R.H., et al., "Structural Requirements of Compounds to Inhibit Pulmonary Diamine Accumulation," *Biochem. Pharmacol.*, 1983, pp. 3701-3709, vol. 32, No. 24, Pergamon Press Ltd., GB.

Gunnia, et al., "Successful Treatment of Lupus Nephritis in MRL-*lpr/lpr* Mice by Inhibiting Ornithine Decarboxylase," *Kidney Int.*, 1991, pp. 882-890, vol. 39, The International Society of Nephrology, Brussels, BE.

Heaton, et al., "Methylglyoxal-bis(guanylhydrazone)-Resistant Chinese Hamster Ovary Cells: Genetic Evidence That More Than a Single Locus Controls Uptake," *J. Cell. Physiol.*, 1988, pp. 133-139, vol. 136, Alan R. Liss, Inc., NY, USA.

Hinuma, K., et al. "Dietary and intestinal polyamines in the rat: in vitro transport studies," In: *Polyamines in the Gastrointestinal Tract*, edited by R.H. Dowling, U.R. Fölsch and C. Löser, 1992, pp. 463-472, Dordrecht: Kluwer Academic Publ., USA and NL.

Itoh, Masumi, et al., "Peptides. VI. Some Oxime Carbonates as Novel *t*-Butoxycarbonylating Reagents," *Bull. Chem. Soc. Jpn.* 1977, pp. 718-721, vol. 50, No. 3, JP.

Jasnis, et al., "Polyamines Prevent DFMO-Mediated Inhibition of Angiogenesis," *Cancer Lett.*, 1994, pp. 39-43, vol. 79, Elsevier Science Ireland Ltd., IE.

Johnson, T. David, "Modulation of Channel Function by Polyamines," *Trends Pharmacol. Sci.*, Jan. 1996, pp. 22-27, vol. 17, Elsevier Science Ltd., NL.

Kabra, et al., "Solid-Phase Extraction and Determination of Dansyl Derivatives of Unconjugated and Acetylated Polyamines by Reversed-Phase Liquid Chromatography: Improved Separation Systems for Polyamines in Cerebrospinal Fluid, Urine and Tissue," *J. Chromatogr.*, 1986, pp. 19-32, vol. 380, .Elsevier Science Publishers B.V., Amsterdam, NL.

Kakinuma, Yoshimi, et al., "Characterization of the Inducible Polyamine Transporter in Bovine Lymphocytes," *Eur. J. Biochem.*, 1988, pp. 409-414, vol. 176, Blackwell Science, DE.

Kohn, Elise, et al., "Clinical Investigation of a Cytostatic Calcium Influx Inhibitor in Patients with Refractory Cancers," *Cancer Res.*, Feb. 1, 1996, pp. 569-573, vol. 56, American Association for Cancer Research, Baltimore, MD, USA.

Komori, Toshihiko, et al., "Norspermidine Inhibits LPS-induced Immunoglobulin Production in an FCS-Independent Mechanism Different from Spermidine and Spermine," *Int. J. Immunopharmacol.*, 1991, pp. 67-73, vol. 13, No. 1, Pergamon Press plc./International Society for Immunopharmacology, GB.

Lee, Younghee, et al., "Reaffirmation That Metabolism of Polyamines by Bovine Plasma Amine Oxidase Occurs Strictly at the Primary Amino Termini," *J. Biol. Chem.*, Jul. 31, 1998, pp. 19490-19494, vol. 273, No. 31, The American Society for Biochemistry and Molecular Biology, Inc., USA.

Li, Albert P., et al., "A comprehensive approach for drug safety assessment," *Chem. Biol. Interact.* 2004, pp. 27-33, vol. 150, Elsevier Ireland Ltd., IE.

Li, Jun, et al., "The pre-ischaemic neuroprotective effect of a novel polyamine antagonist, $N^1$-dansyl-spermine in a permanent focal cerebral ischaemia model in mice," *Brain Res.*, 2004, pp. 84-92, vol. 1029, Elsevier B.V., NL.

Lu, Zhe, "Mechanism of Rectification in Inward-Rectifier $K^+$ Channels," *Annu. Rev. Physiol.*, 2004, pp. 103-130; Annual Reviews, Palo Alto, CA, USA.

Matsufuji, Senya, et al., "Reading two bases twice: mammalian antizyme frameshifting in yeast," *EMBO J.*, 1996, pp. 1360-1370, vol. 15, No. 6, Oxford University Press, Oxford, England.

McCullough, Ph.D., Jerry L., et al., "Regulation of Epidermal Proliferation in Mouse Epidermis by Combination of Difluoromethyl Ornithine (DFMO) and Methylglyoxal Bis(guanylhydrazone) (MGBG)," *J. Invest. Dermatol.*, 1985, pp. 518-521, vol. 85, The Williams & Wilkins Co., USA.

Merali, Salim, "*Pneumocystis carinii* Polyamine Catabolism," *J. Biol. Chem.*, Jul. 23, 1999, pp. 21017-21022, vol. 274, No. 30, The American Society for Biochemistry and Molecular Biology, Inc., USA.

Meyskens, Frank L., et al., "Development of Difluoromethylornithine (DFMO) as a Chemoprevention Agent," *Clin. Cancer Res.*, May 1999, pp. 945-951, vol. 5, The American Association for Cancer Research, USA.

Pohjanpelto, Pirkko, "Putrescine Transport is Greatly Increased in Human Fibroblasts Initiated to Proliferate," *J. Cell Biol.*, 1976, pp. 512-520, vol. 68, Rockefeller University Press, NY, USA.

Porter, Carl W., et al., "Aliphatic Chain Length Specificity of the Polyamine Transport System in Ascites L1210 Leukemia Cells," *Cancer Res.*, Jan. 1984, pp. 126-128, vol. 44, American Association for Cancer Research, USA.

Poulin, Richard, et al., "Stable intracellular acidification upon polyamine depletion induced by α-difluoromethylornithine of $N^1$, $N^{12}$-bis(ethyl)spermine in L1210 leukaemia cells," *Biochem. J.*, 1995, pp. 749-756, vol. 312, Biochemical Society, London, England.

Scalabrino, Giuseppe, et al., "Polyamines in Mammalian Tumors Part 1," In *Adv. Cancer Res.* 1981, pp. 151-268, vol. 35, Academic Press, NY, USA.

Schechter, Paul J., et al., "Clinical Aspects of Inhibition of Ornithine Decarboxylase with Emphasis on Therapeutic Trials of Eflornithine (DFMIO) in Cancer and Protozoan Diseases," In: *Inhibition of Polyamine Metabolism Biological Significance and Basis for New*

*Therapies*, edited by P.P. McCann, A.E. Pegg and A. Sjoerdma, 1987, pp. 345-364, Academic Press, Orlando, FL, USA.

Seiler, Nikolaus, "Acetylation and Interconversion of the Polyamines," In: *The Physiology of Polyamines*, edited by U. Bachrach and Y.M. Heimer, 1989, pp. 159-175, vol. I, CRC Press, Boca Raton, FL, USA.

Seiler, Nikolaus, "Thirty Years of Polyamine-Related Approaches to Cancer Therapy. Retrospect and Prospect. Part 1. Selective Enzyme Inhibitors," *Curr. Drug Targets*, 2003, pp. 537-564, vol. 4, No. 7, Bentham Science Publishers Ltd., NL.

Seiler, Nikolaus, "Thirty Years of Polyamine-Related Approaches to Cancer Therapy. Retrospect and Prospect. Part 2. Structural Analogues and Derivatives," *Curr. Drug Targets*, 2003, pp. 565-585, vol. 4, No. 7, Bentham Science Publishers Ltd., NL.

Simard, Jacques, et al., "Regulation of Progesterone-Binding Breast Cyst Protein GCDFP-24 Secretion by Estrogens and Androgens in Human Breast Cancer Cells: A New Marker of Steroid Action in Breast Cancer," *Endocrinology*, 1990, pp. 3223-3231, vol. 126, No. 6, The Endocrine Society, USA.

Sjoerdsma, M.D., Ph.D., Albert, "Suicide enzyme inhibitors as potential drugs," *Clin. Pharmacol. Therap.*, Jul. 1981, pp. 3-22, vol. 30, No. 1, The C. V. Mosby Co., St. Louis, MO, USA.

Soulet, Denis, et al., "Polyamines play a critical role in the control of the innate immune response in the mouse central nervous system," *J. Cell Biol.*, Jul. 21, 2003, pp. 257-268, vol. 162, No. 2, The Rockefeller University Press, USA.

Taglialatela, Maruzio, et al., "Pharmacological Implications of Inward Rectifier $K^+$ Channels Regulation by Cytoplasmic Polyamines," *Pharmacol. Res.*, 1995, pp. 335-344, vol. 32, No. 6, The Italian Pharmacological Society, IT.

Til, H.P., et al., "Acute and Subacute Toxicity of Tyramine, Spermidine, Spermine, Putrescine and Cadaverine in Rats," *Food Chem Toxicol.*, 1997, pp. 337-348, vol. 35, Elsevier Science Ltd./Pergamon Press, GB.

Tobari, Jiro, et al., "Hydroxyputrescine: 1,4-Diaminobutan-2-ol[1]," *Meth. Enzymol.*, 1983, pp. 431-433, vol. 94, Academic Press, Inc., NY, USA.

Torossian, Krikor, et al., "Substrate protection against inactivation of the mammalian polyamine-transport system by 1-ethyl-3-(3-dimethylaminopropyl)carbodi-imide," *Biochem. J.*, 1996, pp. 21-26, vol. 319, Biochemical Society, GB.

Wallace, H.M., et al., "Inhibitors of polyamine metabolism: Review article," *Amino Acids*, 2004, pp. 353-365, vol. 26, No. 4, Springer, AT.

Weeks, Reitha, S., et al., "Novel Lysine-Spermine Conjugate Inhibits Polyamine Transport and Inhibits Cell Growth When Given with DFMO," *Exp. Cell. Res.*, pp. 293-302, vol. 261, Academic Press, USA.

Williams, Keith, "Interactions of polyamines with ion channels," *Biochem J.*, pp. 289-297, vol. 325, Biochemical Society, GB.

Yarlett, N., "Polyamine Biosynthesis and Inhibition in *Trichomonas vaginalis*," *Parasitol. Today.*, 1988, pp. 357-360, vol. 4, No. 12, Elsevier Science Publishers Ltd., UK.

Yatin, Servet, et al., "Role of Spermine in Amyloid β-Peptide-Associated Free Radical-Induced Neurotoxicity," *J. Neurosci. Res.*, 2001, pp. 395-401, vol. 63, Wiley-Liss, Inc., NY, USA.

Ask, et al., "Antileukemic Effects of Non-Metabolizable Derivatives of Spermidine and Spermine," *Cancer Lett.*, 69: 33-38 (1993).

Ask, et al., "Increased Survival of L1210 Leukemic Mice by Prevention of the Utilization of Extracellular Polyamines. Studies Using a Polyamine-Uptake Mutant, Antibiotics and a Polamine-Deficient Diet," *Cancer Lett.* 66: 29-34 (1992).

Aziz, et al., "A Novel Polymeric Spermine Conjugate Inhibits Polyamine Transport in Pulmonary Artery Smooth Muscle Cells," *J. Pharmacol. Exper. Ther.*, 274 :181-186 (1992).

Aziz, et al., "The Potential of a Novel Polyamine Transport Inhibitor in Cancer Chemotherapy" *Pharmacol. Exper. Ther.* 278 :185-192 (1996).

Bergeron, et al., "Development of a Hypusine Reagent for Peptide Synthesis," *Org. Chem.*, 62: 3285-3290 (1997).

Chaney, et al., "Tumor Selective Enhancement of Radioactivity Uptake in Mice Treated with a α-difluoromethylornithine Prior to Administration of $^{14}C$-putrescine," *Life Sci.*, 32: 1237-1241 (1983).

Chang, et al., "Modulation of Polyamine Biosynthesis and Transport by Oncogene Transfection," *Biochem. Biohphys. Res. Comm.*, 157 :264-270 (1988).

Cohen, et al., "Targeting of Cytotoxic Agents by Polyamines : Synthesis of a Chlorambucil-spermidine Conjugate," *J. Chem. S oc. Chem. Commun.*, pp. 298-300 (1992).

Duranton, et al., "Suppression of Preneoplastic Changes in the Intestine of Rats Fed Low Levels of Polyamines." *Cancer Res* , 57 :573-575 (1997).

Felschow, et al., "Photoaffinity Labeling of a Cell Surface Polyamine Binding Protein" 270 :28705-28711 (1995).

Frebort and Adachi, "Copper/Quinone-Containing Amine Oxidases, an Exciting Class of Ubiquitous Enzymes," *J. Ferment. Bioeng.*, 80 :625-632 (1995).

Hayashi, et al., "Ornithine Decarboxylase Antizyme—A Novel Type of Regulatory Protein," *Trends Biochem. Sci.*, 21 :27-30 (1996).

He, et al., "Antizyme Delays the Restoration by Spermine of Growth of Polyamine-Deficient Cells Through its Negative Regulation of Polyamine Transport," *Biochem. Biophys. Res. Commun.*, 203 :608-614 (1994).

Hessels, et al., "Microbial Flora in the Gastrointestinal Tract Abolishes Cytostatic Effects of α-difluoromethylornithine in vivo," *Int. J. Cancer*, 43 :1155-1164 (1989).

Holley, et al., "Targeting of Tumor Cells and DNA by a Chlorambucil-Spermidine Conjugate," *Cancer Res.*, 52 :4190-4195 (1992).

Horn, et al., "Phase I-II Clinical Trial with α-difluoromethylornithine—an Inhibitor of Polyamine Biosynthesis," *Eur. J. Cancer Clin. Oncol.*, 23:1103-1107 (1987).

Huber and Poulin, "Antiproliferative Effect of Spermine Depletion by -cyclohexyl-1,3-diaminopropane in Human Breast Cancer Cell Growth," *Cancer Res.*, 55 :934-943 (1995).

Huber and Poulin, "Permissive Role of Polyamines in the Cooperative Action of Estrogens and Insulin or Insulin-like Growth Factor I on Human Breast Cancer Cell Growth" *J. Clin. Endocrinol. Metab.* 81 :113-123 (1996).

Huber, et al., "2,2'-Dithiobis(N-ethyl-Spermine-5-Carboximide) is a High Affinity, Membrane-Impermeant Antagonist of the Mammalian Polyamine Transport System," *J. Biol. Chem.*, 271 :27556-27563 (1996).

Janne, et al., "Polyamines from Molecular Biology to Clinical Applications," *Ann. Med.*, 23 :241-259 (1991).

Kanter, et al., "Preclinical Toxicologic Evaluation of DENSPM ($N^1$, $N^{11}$-diethylnorspermine) in Rats and Dogs," *Anti-Cancer Drugs*, 5 :448-456 (1994).

Lakanen, et al., "α-Methyl Polyamines : Metabolically Stable Spermidine and Spermine Mimics Capable of Supporting Growth in Cells Depleted of Polyamines," *J. Med. Chem.*, 35 :724-734 (1992).

Lessard, et al., "Hormonal and Feedback Regulation of Putrescine and Spermidine Transport in Human Breast Cancer Cells," *J. Biol. Chem.*, 270 :1685-1694 (1995).

Li, et al., "Comparative Molecular Field Analysis-based Predictive Model of Structure-Function Relationships of Polyamine Transport Inhibitors in L1210 Cells," *Cancer Res.*, 57 :234-239 (1997).

Love, et al., "Randomized phase I Chemoprevention Dose-seeking Study of α-difluoromethylornithine," *J. Natl. Cancer Inst.*, 85 :732-737 (1993).

Marton and Pegg, "Polyamines as Targets for Therapeutic Intervention," *Ann. Rev. Pharmacol. Toxicol.*, 35 :55-91 (1995).

Matsumoto and Suzuki, "Polyamines as Markers of Malignancy," In :*The Physiology of Polyamines*, edited by U. Bachrach and Y.M. Heimer, Boca Raton, FL : CRC Press, 219-234 (1989).

McCann and Bitonti, "An Overview of Inhibition of Polyamine Metabolism and the Consequent Effects on Cell Proliferation in Mammalian Cells and Parasitic Protozoa," *Polyamines in the Gastrointestinal Tract*, edited by R.H. Dowling, U.R. Folsch and C. Loser, Dordrecht :Kluwer Academic Publ. 143-153 (1992).

McCann and Pegg, "Ornithine Decarboxylase as an Enzyme Target for Therapy," *Pharmac. Ther.*, 54 :195-215 (1992).

McCormack and Johnson, "Putrescine Uptake and Release by Colon Cancer Cells," *Am. J. Physiol.*, 256 :G868-G877 (1989).

Meyskens and Gerner, "Development of Difluoromethyl-ornithine as Chemoprevention Agent for the Management of Colon Cancer," *J. Cell. Biochem.*, 22:126-131 (1995).

Minchin, et al., "Inhibition of Putrescine Uptake by Polypyridinium Quaternary Salts in B16 Melanoma Cells Treated with Difluoromethylornithine," *Biochem. J.*, 262:391-395 (1989).

Mitchell, et al., "Feedback Repression of Polyamine Transport is Mediated by Antizyme in Mammalian Tissue Culture Cells," *Biochem. J.*, 299:19-22 (1994).

Mitchell, et al., "Feedback Repression of Polyamine Uptake into Mammalian Cells Require Active Protein Synthesis," *Biochem. Biophys. Res. Commun.*, 186:81-88 (1992).

Morgan, "Polyamine Oxidases and Oxidized Polyamines," In: *The Physiology of Polyamines*, edited by U. Bachrach and U.M. Heimer. Boca Raton, FL:CRC Press, p. 203-229 (1989).

Moulinoux, et al., "Biological Significance of Circulating Polyamines in Oncology," *Cell. Mol. Biol.*, 37:773-783 (1991).

Moulinoux, et al., "The Growth of MAT-LyLu Rat Prostatic Adeno-Carcinoma Can be Prevented in vivo by Polyamine Deprivation," *J. Urol.*, 146:1408-1412 (1991).

Nicolet, et al., "Putrescine and Spermidine Uptake is Regulated by Proliferation and Dexamethasone Treatment in AR4-2J Cells," *Int. J. Cancer*, 49:577-581 (1991).

O'Sullivan, et al., "Inhibiting Effects of Spermidine Derivatives on *Trypansoma cruzi* Trypanothione Reductase," *J. Enzym Inhib.*, 11:97-114 (1996).

Osborne and Seidel, "Gastrointestinal Luminal Polyamines: Cellular Accumulation and Enterohepatic Circulation," *Am. J. Physiol*,258:G576-G584 (1990).

Parchment, et al., "Serum Amine Oxidase Activity Contributes to Crisis in Mouse Embryo Cell Lines," *Proc. Natl. Acad. Sci.*, USA 87:4340-4344 (1990).

Pegg, et al., "Effect of S-Adenosyl-1, 12-diamino-3-thio-9-azadodecane, a Multisubstrate Adduct Inhibitor of Spermine Synthase, on Polyamine Metabolism in Mammalian Cells," *Biochemistry*, 28:8446-8453 (1989).

Pegg, et al., "Inhibition of Polymaine Biosynthesis and Function as an Approach to Drug Design," *Enzymes as Targets for Drug Design*, edited by M.G. Palfreyman, P.P. McCann, W. Lovenberg, J.G. Temple, Jr. and A. Sjoerdsma. Orlando:Academic Press, 157-183 (1989).

Pegg, et al, "Use of Aminopropyltransferase Inhibitors and of Non-metabolizable Analogs to Study Polyamine Regulation and Function," *Int. J. Biochem Cell Biol.*, 27:425-442 (1995).

Persson, et al., "Curative Effect of DL-2 Difluoromethylornithine on Mice Bearing Mutant L1210 Leukemia Cells Deficient in Polyamine Uptake," *Cancer Res.* 48:4807-4811 (1988).

Porter and Bergeron, "Spermidine Requirement for Cell Proliferation in Eukaryotic Cells: Structural Specificity and Quantitation," *Science*, 219:1083-1085 (1983).

Porter, et al., "Antitumor Activity of $N^1$, $N^{11}$ -bis(ethyl)norspermine Against Human Melanoma Xenografts and Possible Biochemical Correlates of Drug Action," *Cancer Res.* 53:581-586 (1993).

Porter, et al., "Biological Properties of $N^4$ spermidine Derivatives and Their Potential in Anticancer Chemotherapy," *Cancer Res.*, 42:4072-4078 (1982).

Porter, et al., "Biological Properties of $N^4$-and $N^1$, $N^8$-spermidine Derivatives in Cultured L1210 Leukemia Cells," *Cancer Res.*,45:2050-2057 (1985).

Porter, et al., "Collateral Sensitivity of Human Melanoma Multidrug-resistant Variants to the Polyamine Analogue, $N^1$, $N^{11}$ Diethylnorspermine," *Cancer Res.*, 54:5917-5924 (1994).

Porter, et al., "Polyamine Inhibitors and Analogues as Potential Anti-cancer Agents," *Polyamines in the Gastrointestinal Tract*, edited by R.H. Dowling, U.R. Folsch and C. Loser. Dordrecht Kluwer Academic Publ., 301-322 (1992).

Poulin, et al., "Dependence of Mammalian Putrescine and Spermidine Transport on Membrane Potential: Identification of an Amiloride Binding Site on the Putrescine Carrier," *Biochem. J.*, 330;1283-1291 (1998).

Pusztai, et al., "Stimulation of Growth and Polyamine Accretion in the Small Intestine and Pancreas by Lectins and Trypsin Inhibitors," *Polyamines in the Gastrointestinal Tract*, edited by R.H. Dowling, U.R. Folsch and C. Loser. Dordrecht:Kluwer Academic Publ., 473-483 (1992).

Quemener, et al., "Polyamine Deprivation: a New Tool in Cancer Treatment," *Anticancer Res.* 14:443-448 (1994).

Quemener, et al., "Tumour Growth Inhibition by Polyamine Deprivation," *Polyamines in the Gastrointestinal Tract*, edited by R.H. Dowling, U.R. Folsch and C. Loser, Dordrecht:Kluwer Academic Publ. 375-385 (1992).

Rinehart and Chen, "Characterization of the Polyamine Transport System in Mouse Neuroblastoma Cells," *J. Biol. Chem.*,259:4750-4756 (1984).

Sarhan, et al., "The Gastrointestinal Tract as Polyamine Source for Tumor Growth," *Anticancer Res* 9:215-224 (1989).

Schechter, et al., "Clinical Aspects of Inhibition of Ornithine Decarboxylase with Emphasis on Therapeutic Trials on Eflornithine (DFMIO) in Cancer and Protozoan Diseases," *Inhibition of Polyamine Metabolism. Biological Significance and Basis for New Therapies*, edited by P.P. McCann, A.E. Pegg and A. Sjoerdsma. Orlando, FL: Academic Press, 345-364 (1987).

Seiler and Dezeure, "Polyamine Transport in Mammalian Cells," *Int. J. Biochem.* 22:211-218 (1990).

Seiler, et al., "Endogenous and Exogenous Polyamines in Support of Tumor Growth," *Cancer Res* 50:5077-5083 (1990).

Seiler, et al., "Polyamine Transport in Mammalian Cells. An Update," *Int. J. Biochem.*, 28:843-861 (1996).

Seiler, "Polyamine Catabolism and Elimination by the Vertebrate Organism," *Polyamines in the Gastrointestinal Tract*, edited by R.H. Dowling, U.R. Folsch and C. Loser. Dordrecht:Kluwer Academic Publ. 65-85 (1992).

Sjoerdsma and Schechter, "Chemotherapeutic Implication of Polyamine Biosynthesis Inhibition," *Clin. Pharm. Thera.* 35(3):287-300 (1984).

Sjoerdsma and Schechter, "Successful Treatment of Lethal Protozoal Infections with the Ornithine Decarboxylase Inhibitor, α-dilfuoromethylornithine," *Trans. Ass. Am. Physic.*, 97:70-79 (1984).

Stark, et al., "Synthesis and Evaluation of Novel Spermidine Derivatives as Targeted Cancer Chemotherapeutic Agents," *J. Med. Chem.*, 35:4264-4269 (1992).

Steele, et al., "Preclinical Efficacy Evaluation of Potential Chemopreventive Agents in Animal Carciogenesis:Methods and Results from the NCI Chemoprevention Drug Development Program," *J. Cell. Biochem.*, (suppl) 20:32-54 (1994).

Sunkara, P.S., et al., "Inhibitors of Polyamine Biosynthesis: Cellular and in vivo Effects on Tumor Proliferation," *Inhibition of Polyamine Metaolism Biological Significance and Basis for New Therapies*, edited by edited by P.P. McCann, A.E. Pegg and A. Sjoerdsma. Orlando, FL: Academic Press 121-140 (1987).

Talpaz, et al., "Clinical Studies of α-difluoromethylornithine and α-interferon Combination in Cancer Patients," *The Physiology of Polyamines*, edited by U. Bachrach and Y.M. Heimer, Boca Raton, FL: CRC Press 287-292 (1989).

Tanaka, et al., "Chemoprevention of Oral Carcinogenesis by DL-α-difluoromethylornithine, an Ornithine Decarboxylase Inhibitor: Dose-dependent Reduction in 4-nitroquinoline 1-oxide Induced Tongue Neoplasms in Rats," *Cancer Res.* 53-772-776 (1993).

Tempero, et al., "Chemoprevention of Mouse Colon Tumors with Difluoromethylornithine During and After Carcinogen Treatment," *Cancer Res*, 49:5793-5797 (1989).

Tjandrawinata and Byus, "Regulation of the Efflux of Putrescine and Cadaverine from Rapidly Growing Cultured RAW 264 Cells by Extracellular Putrescine," *Biochem. J.*, 305:291-299 (1995).

Tjandrawinata, et al. "Regulation of Putrescine Export in Lipopolysaccharide of IFN-γ-activated Murine Monocytic-Leukemic RAW 264 Cells," *J. Immunol.*, 152:3039-3052 (1994).

Zang and Sadler, "Synthesis of Hexamine Ligands by Using Trityl as an N-blocking Agent," *Synthetic Communications*, 27:3145-3150 (1997).

Hubsch-Weber, et al., "Synthesis and Characterization of a New Series of [12]aneN$_3$ Type Macrocycles, Structures of two Protonated Metal-Free Ligands," *Tetrahedron Letters*, vol. 38, No. 11 pp. 1911-1914 (1997).

Huber, Maria, et al., "2,2'-Dithiobis (N-ethyl-spermine-5-carboxamide) is a High Affinity, Membrane-Impermeant Antagonist of the Mammalian Polyamine Transport System," *The Journal of Biological Chemistry*, vol. 271, No. 44, pp. 27556-27563 (1996).

Buhleier, Egon, et al., "Cascade"—and "Nonskid-chain-like" *Syntheses of Molecular Cavity Topologies* Georg Thieme Publishers, pp. 155-158 (1978).

* cited by examiner

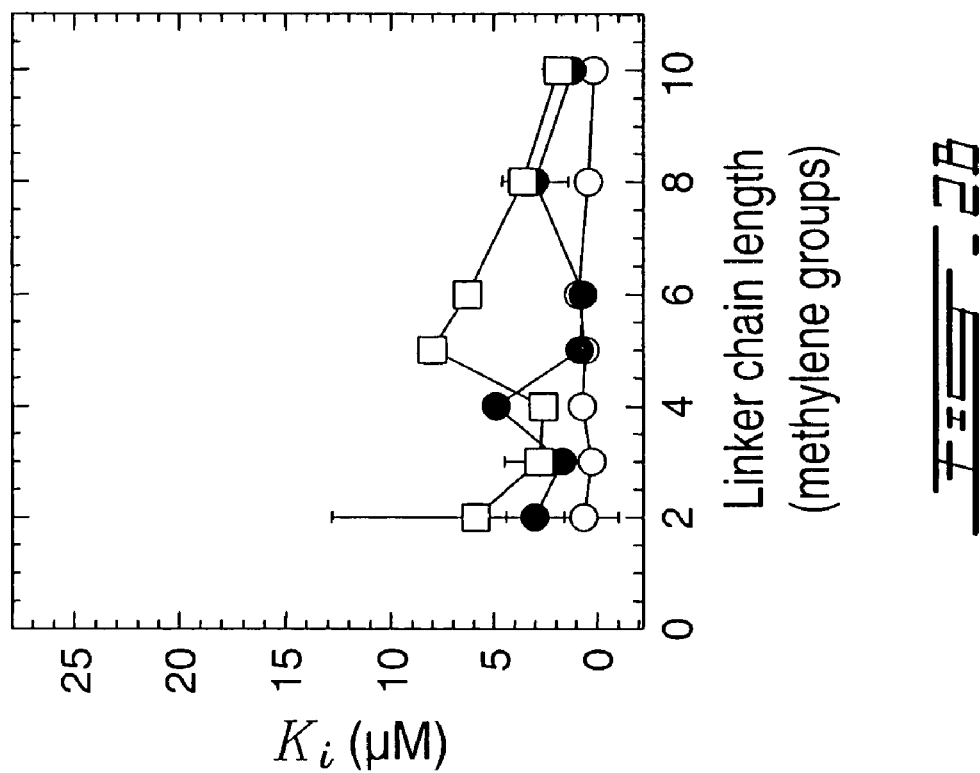
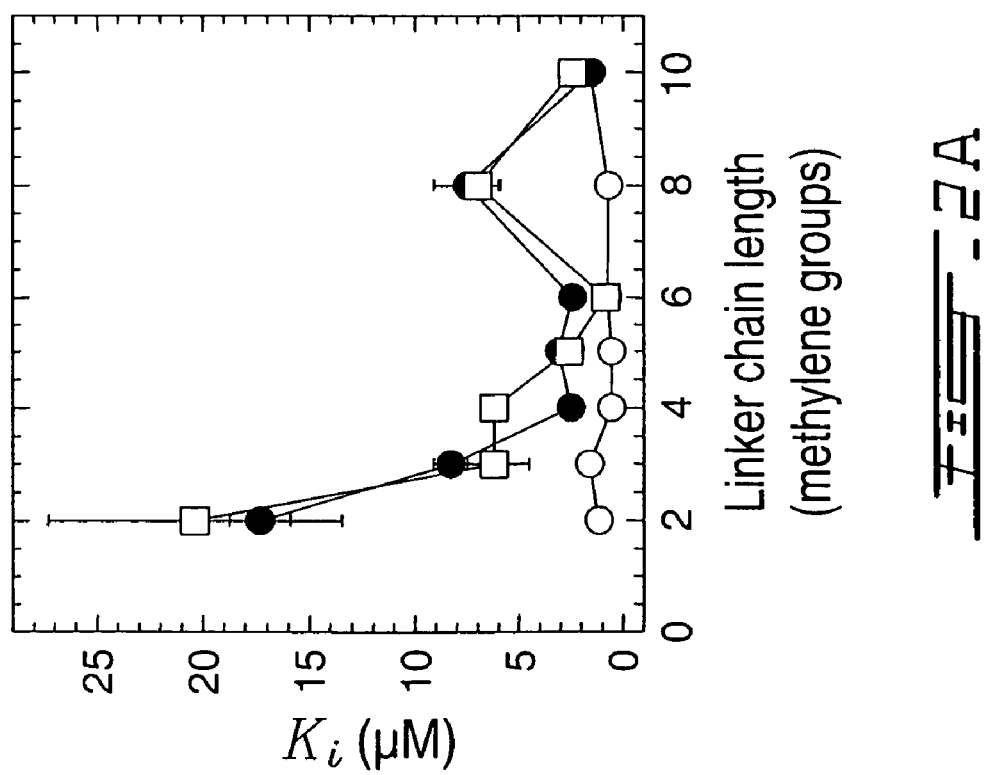
FIG. 2A
FIG. 2B

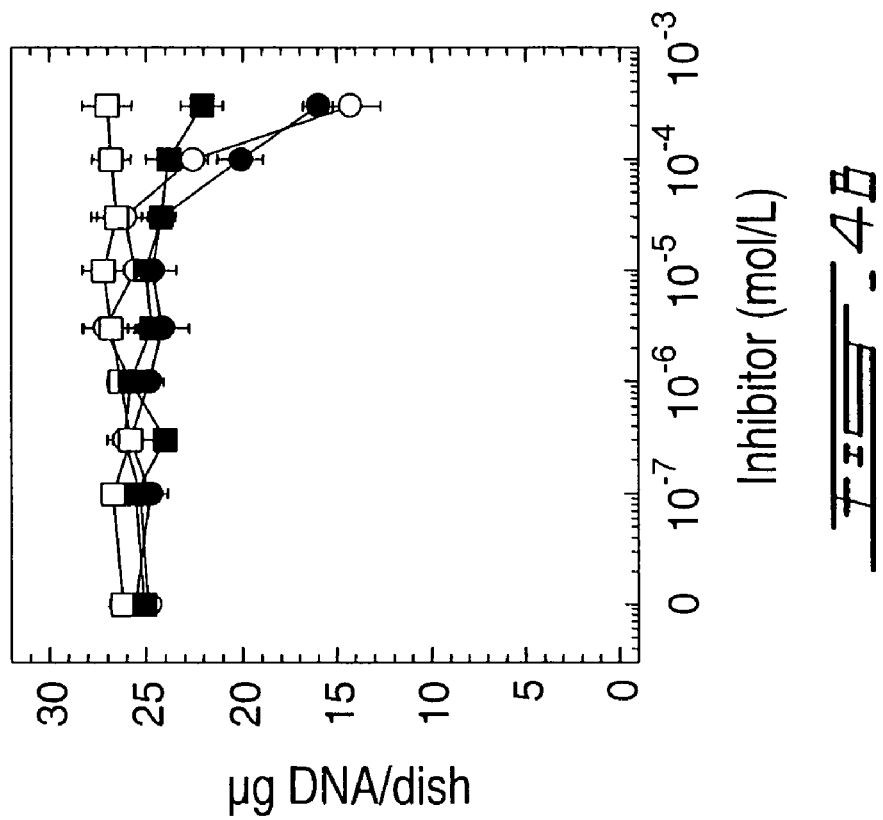
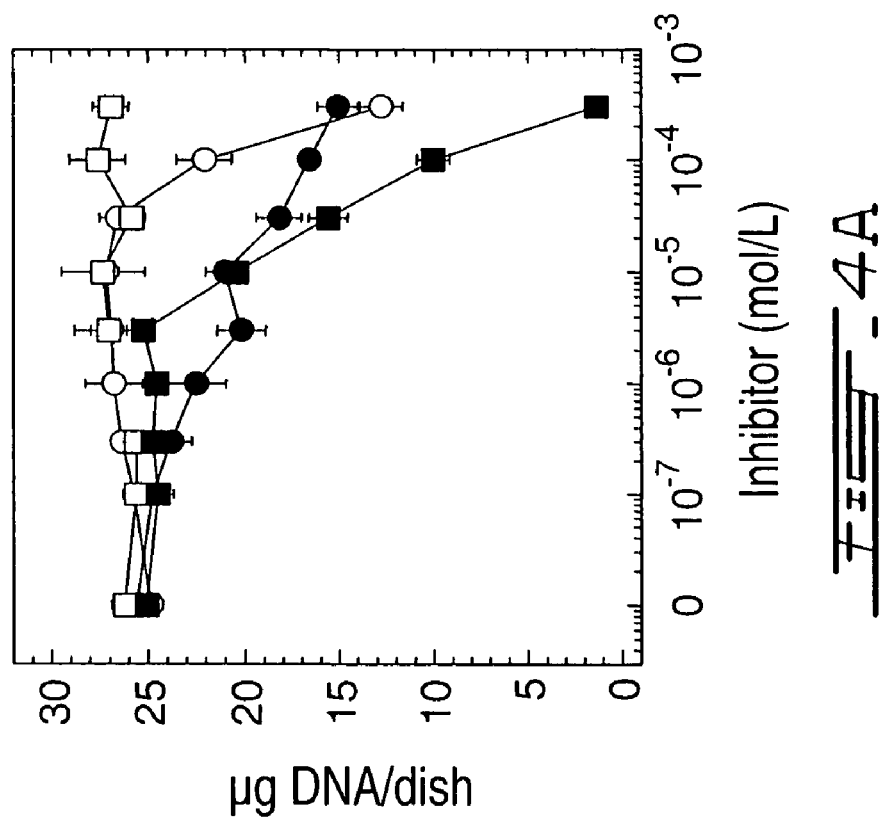
FIG. 4A
FIG. 4B

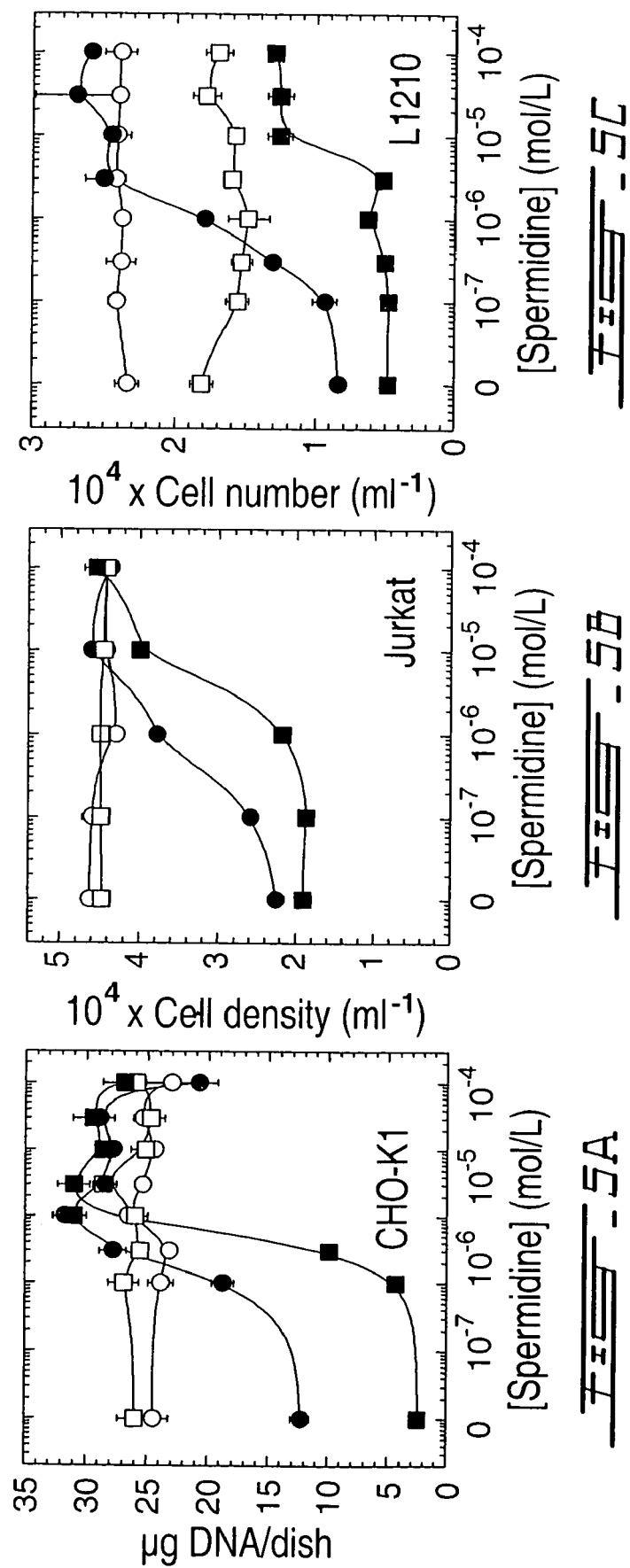

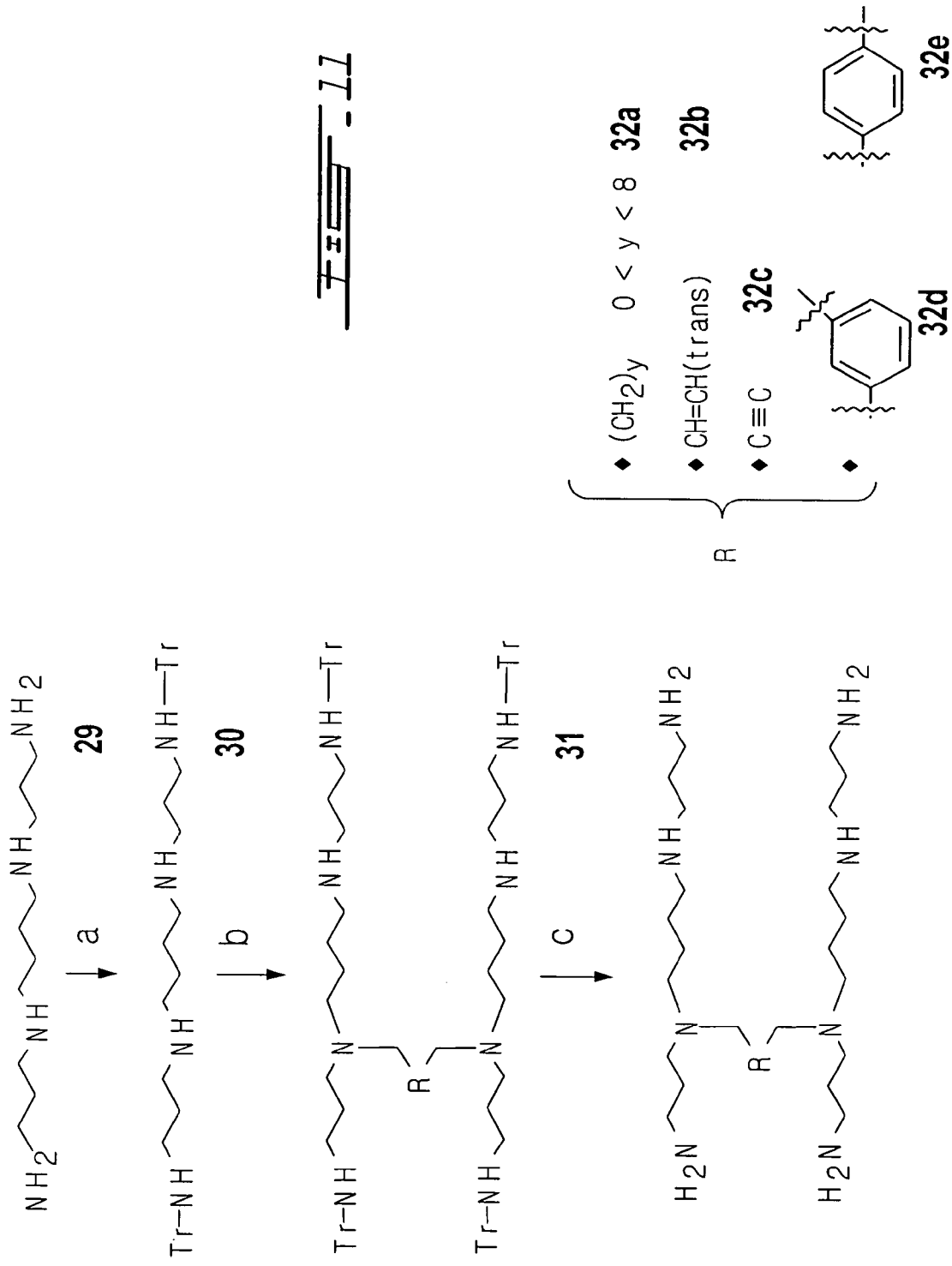

METHODS FOR INHIBITING ACTIVITY OF POLYAMINE TRANSPORTERS

CROSS-REFERENCE TO RELATED APPLICATION

The present application is a continuation-in-part of U.S. non-provisional application Ser. No. 09/529,319 filed on Feb. 9, 2000 now U.S. Pat. No. 6,949,679, which claims priority on PCT/US98/07806 filed on Apr. 21, 1998. The above-mentioned applications are incorporated herein by reference in their entirety.

TECHNICAL FIELD

The present invention relates to improvements in the field of inhibitors for polyamine transporters. In particular, this invention relates to a method for inhibiting the activity of a natural polyamine transporter as well as a method for treating disorder wherein control of polyamine transport is required,

BACKGROUND OF THE INVENTION

The polyamines spermidine and spermine, as well as its precursor, putrescine, are required for numerous cellular functions in mammalian cells, including post-translational modification of eukaryotic initiation factor eIF-5A, ion channel gating, and at several steps of nucleic acid and protein synthesis. Polyamines are synthesized by most cell types, and catalysis of putrescine biosynthesis via ornithine decarboxylase[1] (ODC) is a major rate-limiting step in the polyamine biosynthetic pathway. Polyamines can also be utilized from extracellular sources via one or several membrane carriers (Seiler et al. (1990) *Int. J. Biochem.* 22, 211-218). A number of polyamine carriers of various substrate specificity have been characterized from bacterial species, and a vacuolar polyamine transporter has been identified in the yeast *Saccharomyces cerevisiae*. However, no molecular identification for a plasma membrane transporter specific for polyamines has yet been reported in eukaryotes.

High-affinity mammalian polyamine transport activity is membrane potential-dependent and $Na^+$ gradient-independent, and requires divalent cations (e.g. $Ca^{2+}$, $Mg^{2+}$, $Mn^{2+}$) for its activity (Poulin et al. (1998) *Biochem. J.* 330, 1283-1291). Polyamine uptake is regulated by intracellular polyamines through several feedback mechanisms (Seiler et al. (1990) *Int. J. Biochem.* 22, 211-218), including rapid down-regulation by ODC antizyme via translational frame-shifting (Matsufuji et al. (1996) *EMBO J.* 15, 1360-1370) and up-regulation of its $V_{max}$ upon chronic polyamine depletion (Seiler et al. (1990) *Int. J. Biochem.* 22, 211-218; Lessard et al. (1995) *J. Biol. Chem.* 270, 1685-1694) by agents like α-difluoromethylornithine (DFMO), a suicide substrate of ODC (Lessard et al. (1995) *J. Biol. Chem.* 270, 1685-1694). DFMO is currently commercialized under the trade name of Eflornithine™. Moreover, enhanced polyamine transport is associated with rapid cell proliferation and transformation (Seiler et al. (1990) *Int. J. Biochem.* 22, 211-218).

The absolute polyamine requirement for tumor progression has been the target of promising therapeutic approaches such as the vectorization of cytotoxic polyamine analogs such as $N^1,N^{11}$-diethylnorspermine through the polyamine transport system, or polyamine depletion using DFMO (Marton et al. (1995) *Ann. Rev. Pharmacol. Toxicol.* 35, 55-91). The latter approach is currently considered as a potentially effective treatment for chemoprevention of various cancers in human (Gerner et al. (2004) *Nat Rev Cancer.* 4:781-792). In addition to promoting cytostasis, polyamine depletion through the use of DFMO inhibits angiogenesis and metastasis (Jasnis et al. (1994) *Cancer Lett.* 79, 39-43). Although most tumor cell types enter growth arrest upon treatment with DFMO, the in vivo therapeutic efficacy of DFMO has been limited to isolated cases (Jasnis et al. (1994) *Cancer Lett.* 79, 39-43; Marton et al. (1995) *Ann. Rev. Pharmacol. Toxicol.* 35, 55-91). There is substantial evidence that the antitumor action of DFMO is severely impaired by the high-affinity capture of plasma polyamines by tumor cells. For instance, tumors formed by polyamine transport-deficient cells are much more sensitive to DFMO in mice than in the case of the parental strain (Persson et al. (1988) *Cancer Res.* 48, 4807-4811). Moreover, polyamine deprivation by decontamination of the gastrointestinal tract or by feeding a polyamine-poor diet can markedly decreases tumorigenesis and enhance DFMO-induced inhibition tumor progression in vivo (Seiler et al. (1990) *Int. J. Biochem.* 22, 211-218). Concentrations of polyamines similar to those found in human plasma (0.1-1 μM) are in fact sufficient to completely antagonize the effect of DFMO in human breast cancer cells (U.S. Pat. No. 6,083, 496).

Limitation of DFMO action by the high polyamine transport activity found in tumor cells could in principle be alleviated by the use of drugs interfering with polyamine uptake. Such drugs should be endowed with high affinity toward the polyamine carrier and low cytotoxicity, and be poorly cell-permeant (U.S. Pat. No. 6,083,496) in order to preserve the therapeutic benefits of DFMO-induced polyamine depletion (Marton et al. (1995) *Ann. Rev. Pharmacol. Toxicol.* 35, 55-91). Only few attempts have previously been made to design specific inhibitors of polyamine transport. Linear polypyridinium compounds designed as paraquat surrogates are highly potent inhibitors of putrescine transport (Minchin et al. (1989) *Biochem. J.* 262, 391-395) but their ability to compete for spermidine or spermine uptake has not been reported. More recently, a high $M_r$ (≈25,000) spermine polymer has been shown to be a high-affinity competitor of diamine and polyamine transport (Aziz et al. (1996) *J. Pharmacol. Exper. Ther.* 278, 185-192), but its high cytotoxicity is probably the main factor involved in its antitumor action.

Applicants have previously showed that 2,2'-dithiobis(N-ethyl-spermine-5-carboxamide) (DESC), obtained through dimerization of two N-(2-mercaptoethyl) spermine 5-carboxamide moieties through a disulfide bridge, leads to a potent cell-impermeant polyamine transport antagonist with a much lower $K_i$ than the parent monomer (U.S. Pat. No. 6,083,496). These results were encouraging but some improvement could be interesting in this particular field.

SUMMARY OF THE INVENTION

It is therefore an object of the present invention to overcome the above-mentioned drawbacks.

According to one aspect of the invention, there is provided a method for inhibiting the activity of a natural polyamine transporter comprising the step of contacting said transporter with an inhibitorily effective amount of a compound of formula (I) or (II):

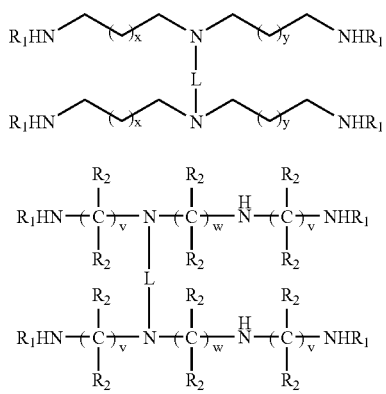

wherein
L is:

R₁=H, methyl, ethyl or propyl;
R₂=H or methyl;
$0<x<3$;
$0<y<3$;
$0<i<6$;
$0<j<6$;
$1<i+j<7$;
$2<v<5$; and
$2<w<8$.

It has been found that such a method is very effective for inhibiting polyamine transport. In particular, such a method is very effective for promoting the extensive depletion of polyamines such as putrescine, spermidine, or spermine. In fact, it has been shown that such a method permit to potently inhibit polyamines transport in cultured mammalian cancer cells. Therefore, such method can permit to inhibit polyamine transport, thereby efficiently preventing rescue of an inhibitor of polyamine synthesis-induced growth arrest by exogenous polyamines in mammalian cells. In addition, this method presents extremely low toxic effects toward mammalian cells, both in cultured cells and in whole organisms.

According to another aspect of the invention, there is provided a method for a treating disorder wherein control of polyamine transport is required, said method comprising the step of administering to a patient an inhibitorily effective amount of a compound of formula (I) or (II), as previously defined.

According to another aspect of the invention, there is provided a method for preventing or treating cancer comprising the step of administering to a patient a compound of formula (I) or (II), as previously defined.

In the methods of the present invention L, the linker, can be

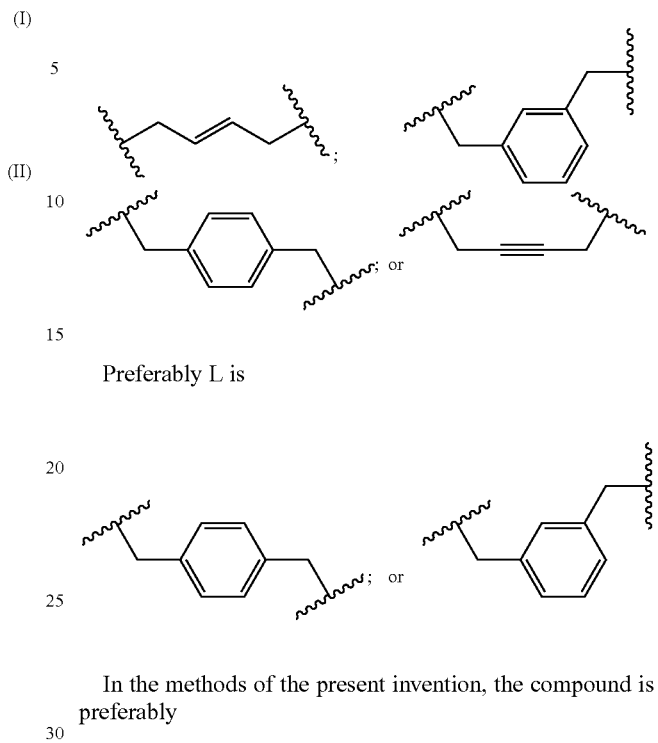

Preferably L is

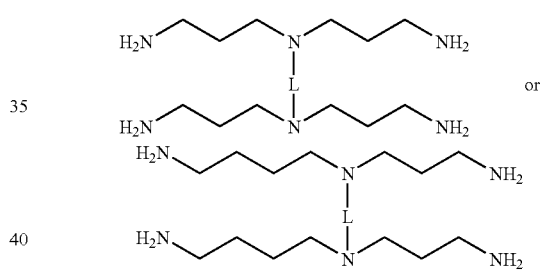

In the methods of the present invention, the compound is preferably wherein L is as previously defined.

In the methods of the present invention, the compound is preferably administered per os to the patient. The compound can also be administered in combination with an inhibitor of polyamine synthesis such as DFMO.

In the method of the present invention for a treating disorder wherein control of polyamine transport is required, the disorder can be selected from the group consisting (i) cancers of various types (such as the various forms of leukemia, myeloma, neuroblastoma, lymphoma, melanoma, and carcinomas of the breast, prostate, stomach, liver, colon, lung, brain, and bladder) and similar neoplastic or pre-neoplastic disorders (such as precancerous cryptic states histologically related to the above list of cancer disorders); (ii) neurodegenerative disorders (such as Alzheimer's disease, Parkinson's disease, amyotrophic lateral sclerosis, and cerebral ischemia); (iii) neuropathological and motor disorders resulting from abnormal cellular excitability (such as epilepsy and ataxia); (iv) autoimmune disorders (such as systemic lupus erythematosus and psoriasis); (v) parasitic infections caused by microorganisms that are sensitive to polyamine depletion (such as infections by *Trypanosoma* spp., *Leishmania* spp., *Plasmodium* spp., *Trichomonas* spp., and *Pneumocystis carinii*); and (vi) hypertrichosis.

In the method of the present invention for preventing or treating cancer, the types of cancer can be cancers of various types (such as the various forms of leukemia, myeloma, neuroblastoma, lymphoma, melanoma, and carcinomas of the breast). It can also be prostate cancer, stomach cancer, liver cancer, colon cancer, lung cancer, brain cancer, and bladder cancer and similar neoplastic and pre-neoplastic disorders (such as precancerous cryptic states histologically related to the above list of cancer disorders).

BRIEF DESCRIPTION OF FIGURES

In the following figures, which represent by way of example only preferred embodiments of the invention.

FIGS. 2A and 2B are graphs showing the effect of the chain length of compounds used in a method according preferred embodiment of the present invention, on polyamine transport inhibition. In particular, the abscissa corresponds to the number of methylene groups present in the linker of the corresponding BNSD (A) or BSD (B) derivative. $K_i$ values for inhibition of [$^3$H]putrescine (○), [$^3$H]spermidine (●) and [$^{14}$C]spermine uptake (□) are taken from Table 1;

FIGS. 4A and 4B are graphs showing how compounds used in a method according to a preferred embodiment are differentially sensitive to degradation by BSAO (bovine serum amine oxidase). In particular, T-47D cells were incubated for 9 d with the indicated concentrations of BSD-X (○), BNSD-X (●), BSD-3 (□) or BNSD-3 (■) in the absence (A) or presence of 1 mM aminoguanidine (B), and total DNA content per culture was then determined. Data are presented as the mean±SD for triplicate cultures from one representative experiment;

FIGS. 5A, 5B, 5C, 5D, 5E and 5F are graphs representing that a compound used in a method according to a preferred embodiment antagonizes rescue of DFMO-induced cytostasis by exogenous spermidine. In particular, CHO-K1 (A), Jurkat (B), L1210 (C), MDA-MB-231 (D), ZR-75-1 (E) and MCF-7 cells (F) were grown to near confluency or saturation (for 4 to 11 d according to the cell line considered) with the indicated concentrations of spermidine in medium containing 1 mM aminoguanidine, in the presence of DFMO (●), BNSD-X (□), DFMO plus BNSD-X (■), or in the absence of either agent (○), and total DNA content per culture was then determined. The optimal concentration of either DFMO (1 to 5 mM) or BNSD-X (50 or 100 μM) was used for the each cell line as determined in pilot experiments. Data are presented as the mean±SD for triplicate cultures from one out of at least three identical experiments for each cell line;

FIG. 11 is a scheme for the synthesis of compounds used in a method according to a preferred embodiment of the invention. In particular, the steps for the synthesis of spermine dimers are detailed as follows: step (a) TrCl, Et$_2$NH, CHCl$_3$; step (b) α,α'-dibromo-p-xylene, K$_2$CO$_3$, DMF (cat), acetonitrile, reflux; step (c) 3 N HCl, reflux;

DESCRIPTION OF PREFERRED EMBODIMENTS

Further features and advantages of the invention will become more readily apparent from the following non-limiting examples, which further illustrate the invention.

EXAMPLES

Materials and Reagents

All reagents for organic synthesis were purchased from Aldrich and Sigma. Silica gel (40 μM; J. T. Baker, Phillipsburg, N.J.) was used for flash column chromatography. [2,3-³H]Putrescine dihydrochloride (3.6×10⁴ Ci/mol) and [1,8-³H]spermidine trihydrochloride (4.1×10⁴ Ci/mol) were obtained from DuPont-NEN (Mississauga, Ontario). [5,8-¹⁴C]Spermine tetrahydrochloride (100-120 Ci/mol) was obtained from Amersham Life Science (Oakville, Ontario). DFMO was a generous gift from ILEX Oncology Inc. (San Antonio, Tex.). Fetal bovine serum (FBS) and Cosmic™ calf serum were purchased from Hyclone (Logan, Utah). Other biochemical and tissue culture reagents were from Sigma. CHO-MG cells (Heaton et al. (1988) *J. Cell. Physiol.* 136, 133-139) and their parental strain (CHO-TOR) were kindly provided by Dr. Wayne Flintoff (University of Western Ontario, London, Ont., Canada).

General Methods for Organic Synthesis

Homogeneity of protected synthetic products was assessed by thin layer chromatography performed on 0.25-mm silica gel 60 F$_{254}$ plates (E. Merck, Darmstadt, Germany). Purity of deprotected compounds was confirmed by ion pairing reverse phase high performance liquid chromatography with post-column derivatization with o-phthaldialdehyde and on-line fluorometric detection as described (U.S. Pat. No. 6,083,496). $^1$H and $^{13}$C NMR spectra were recorded on a Bruker 300 spectrometer. Chemical shift values (δ in ppm) are given relative to CHCl$_3$ (7.26 ppm) for $^1$H and CDCl$_3$ (77 ppm) for $^{13}$C.

Protection of Primary Amino Groups of Spermidine and Norspermidine

Figure 1:
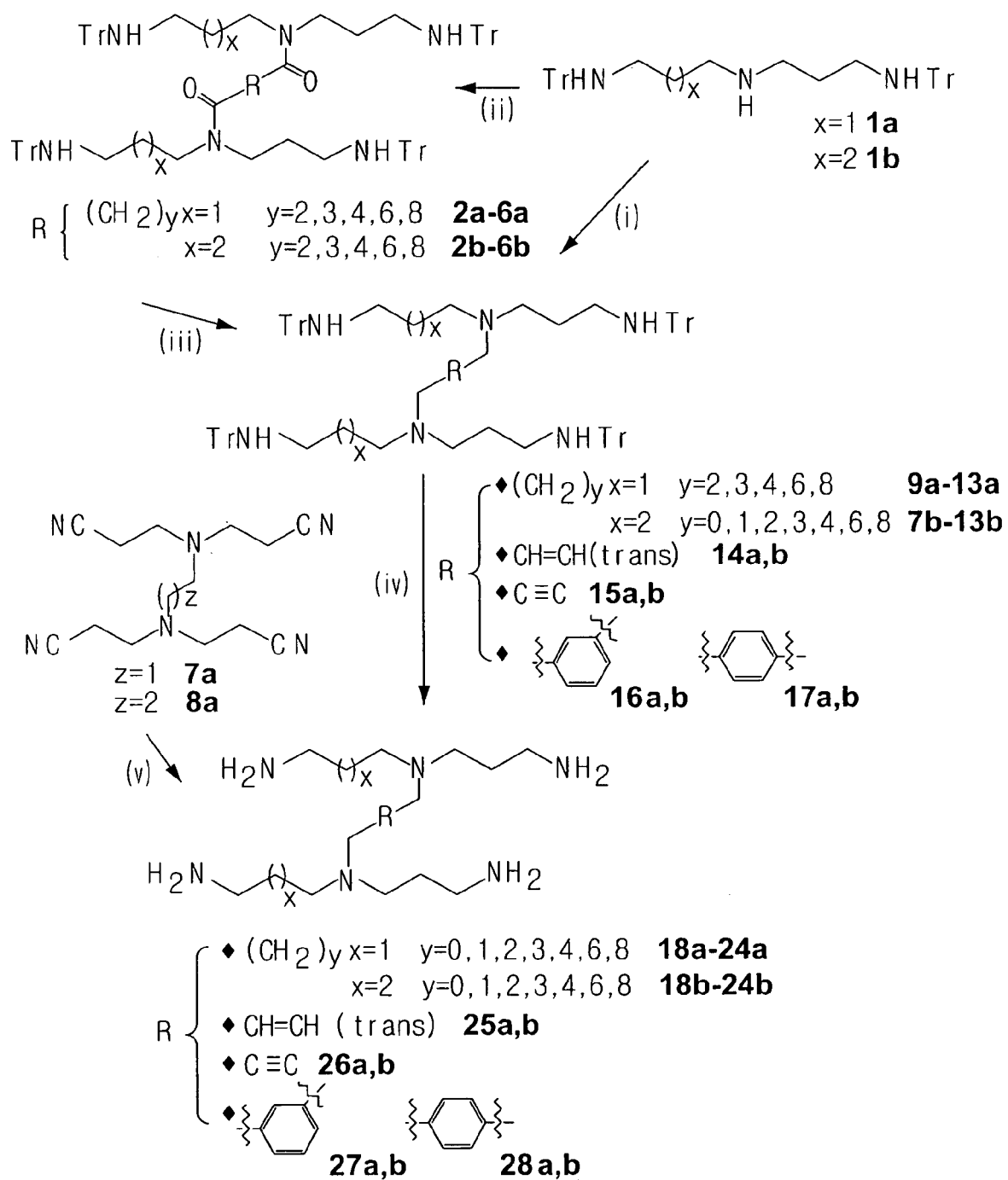
FIG. 1A shows a scheme for the synthesis of compounds used in a method according to a preferred embodiment of the invention. In particular, the steps for the synthesis of spermidine dimers (BSD) and norspermidine dimers (BNSD) are detailed as follows: step (i), ditosylate or dihalide/$K_2CO_3$/acetonitrile; step (ii), diacyl chloride/triethylamine/$CHCl_3$, 0° C.; step (iii), $LiAlH_4$/dry THF; step (iv) 3 M HCl, reflux; step (v), NaOH/EtOH/Raney nickel/$H_2$.

The first step in the synthesis (see FIG. 1) of all triamine dimers (except for compounds 18a and 19a; see below) involved protection of the primary amino groups of spermidine or norspermidine in their free base form with trityl groups (FIG. 1). Briefly, a solution of norspermidine or spermidine (1 equiv) and diethylamine (4 equiv) in anhydrous CHCl$_3$, was slowly added to a solution of trityl chloride (2 equiv) in CHCl$_3$ at room temperature (Covassin et al. (1999) *Bioorg. Med. Chem. Lett.* 9, 1709-1714). Diethylamine was found to be more efficient than triethylamine to prevent tritylation of the secondary amino group of the parent triamine. The reaction mixture was stirred overnight, then washed twice with brine and dried over K$_2$CO$_3$. The solvent was removed and the residue diluted in the minimal amount of CH$_2$Cl$_2$ followed by addition of a large amount of boiling MeOH to perform the recrystallization. The desired N$^α$,N$^ω$-bis(trityl) derivatives of spermidine and norspermidine were obtained in approximately 70% yield: 1a: $^1$H NMR (CDCl$_3$): δ 7.46 (m, 12H, aromatic-H), 7.12-7.30 (m, 18H, aromatic-H), 2.36 (t, 4H, J=8 Hz, 2×CH$_2$N), 2.18 (t, 4H, J=8 Hz, 2×CH$_2$N), 1.66 (m, 6H, 2×CH$_2$; 2×NH); 1b: m.p. 137° C.; $^1$H NMR (CDCl$_3$): δ 7.4-7.5 (m, 12H, aromatic-H), 7.2-7.3 (m, 12H, aromatic-H), 7.15-7.2 (m, 6H, aromatic-H), 2.6 and 2.7 (2t, 4H, 2×CH$_2$N), 2.1 and 2.2 (2t, 4H, 2×CH$_2$N), 1.7 (m, 2H, CH$_2$), 1.6 (m, 6H, 2×CH$_2$; 2×NH).

Dimerization of N$^1$,N$^9$-bis(trityl)spermidines and N$^1$,N$^8$-bis(trityl)norspermidines The second step (see FIG. 1) in the synthesis of final compounds 18b, 19b, 25a-b, 26a-b, 27a-b and 28a-b involved direct alkylation of the secondary amino nitrogen of N$^1$,N$^9$-bis(trityl)spermidine or N$^1$,N$^8$-bis(trityl)norspermidine with the appropriate ditosylate or dihalide form of the desired crosslinker. The tritylated dimers 16a-b and 17a-b were synthesized by alkylation with the appropriate dibromides, whereas 14a-b and 15a-b were obtained from the dichlorides; the various dihalides used were available commercially (Aldrich, Milwaukee, Wis.). The tritylated intermediates 7b and 8b were synthesized by coupling with ethyl ditosylate and propyl ditosylate, which were prepared from ethylene glycol and 1,3-propanediol, respectively. Briefly, to a solution of the diol in anhydrous CHCl$_2$ was added p-tosyl chloride (2.2 equiv) and pyridine (2.4 equiv). The reaction mixture was stirred overnight under N$_2$ and then filtered. The filtrate was washed twice with 1 N HCl then brine, dried over K$_2$CO$_3$ and concentrated to dryness. Recrystallization from MeOH afforded the pure compound in 50% yield. ($^1$H NMR (CDCl$_3$)): TsO(CH$_2$)$_2$OTs δ 7.75 and 7.35 (2d, 8H, aromatic-H), 4.05 (s, 4H, 2×CH$_2$OTs), 2.45 (s, 6H, 2×CH$_3$); TsO (CH$_2$)$_3$OTs δ 7.75 and 7.35 (2d, 8H, aromatic-H), 4.05 (t, 4H, 2×CH$_2$OTs), 2.45 (s, 6H, 2×CH$_3$), 2.0 (q, 2H, CH$_2$).

A mixture containing 1a or 1b, dihalide or ditosylate (0.48 equiv), anhydrous K$_2$CO$_3$ (4.2 equiv) and acetonitrile (16 ml/g of amine) was refluxed for 5 days. The mixture was then evaporated to dryness, and taken up in CHCl$_3$. The organic layer was washed with water, dried over anhydrous K$_2$CO$_3$ and again concentrated. Purification by flash column chromatography using silica gel pretreated with triethylamine and eluted with AcOEt/petroleum ether 1/1 gave the pure compounds in yields varying from 90 to 95%. $^1$H NMR (CDCl$_3$): 7b δ 7.6 (m, 24H, aromatic-H), 7.2-7.4 (m, 36H, aromatic-H), 2.4-2.6 (m, 12H, 6×CH$_2$N$^{III}$), 2.05 (m, 8H, 4×CH$_2$N$^{II}$), 1.7 (m, 4H, 2×CH$_2$), 1.55 (m, 8H, 4×CH$_2$); 8b δ 7.6 (m, 24H, aromatic-H), 7.2-7.4 (m, 36H, aromatic-H), 2.5-2.65 (m, 8H, 4×CH$_2$N$^{III}$), 2.25 (m, 4H, 2×CH$_2$N$^{III}$), 2.1 (m, 8H, 4×CH$_2$N$^{II}$), 1.4-1.8 (m, 12H, 6×CH$_2$); 14a δ 7.4-7.5 (m, 24H, aromatic-H), 7.1-7.3 (m, 36H, aromatic-H), 5.48 (s, 2H, CH=CH), 3.01 (s, 4H, 2×CH$_2$N$^{III}$), 2.40 (m, 8H, 4×CH$_2$N$^{III}$), 2.08 (m, 8H, 4×CH$_2$N$^{II}$), 1.85 (br s, 4H, 4×NH), 1.4 (m, 8H, 4×CH$_2$); 14b δ 7.55 (m, 24H, aromatic-H), 7.1-7.4 (m, 36H, aromatic-H), 5.5 (m, 2H, CH=CH), 3.0 (m, 4H, 2×CH$_2$N$^{III}$), 2.3-2.5 (m, 8H, 4×CH$_2$N$^{III}$), 2.1 (m, 8H, 4×CH$_2$N$^{II}$), 1.6 (m, 4H, 2×CH$_2$), 1.4 (m, 8H, 4×CH$_2$); 15a δ 7.4-7.5 (m, 24H, aromatic-H), 7.1-7.3 (m, 36H, aromatic-H), 3.38 (s, 4H, 2×CH$_2$N$^{III}$), 2.41 (t, 8H, 4×CH$_2$N$^{III}$, J=6.8 Hz), 2.12 (t, 8H, 4×CH$_2$N$^{II}$, J=6.4 Hz), 1.76 (br s, 4H, 4×NH), 1.55 (m, 8H, 4×CH$_2$); 15b δ 7.45 (m, 24H, aromatic-H), 7.1-7.3 (m, 36H, aromatic-H), 3.35 (m, 4H, 2×CH$_2$N$^{III}$), 2.25-2.45 (m, 8H, 4×CH$_2$N$^{III}$), 2.1 (m, 8H, 4×CH$_2$N$^{II}$), 1.6 (m, 8H, 2×CH$_2$, 4×NH), 1.4 (m, 8H, 4×CH$_2$); 16a δ 7.4-7.5 (m, 24H, aromatic-H), 7.1-7.3 (m, 36H, aromatic-H), 3.35 (bs, 4H, 2×CH$_2$), 2.40 (m, 8H, 4×CH$_2$N$^{III}$), 2.10 (m, 8H, 4×CH$_2$N$^{II}$), 1.5-1.8 (m, 12H, 4×CH$_2$, 4×NH); 16b δ 7.6 (m, 24H, aromatic-H), 7.15-7.4 (m, 36H, aromatic-H), 3.55 (s, 4H, 2×CH$_2$), 2.4-2.6 (m, 8H, 4×CH$_2$N$^{III}$), 2.25 (m, 8H, CH$_2$N$^{II}$), 1.8 (m, 4H, 2×CH$_2$), 1.55 (m, 12H, 4×CH$_2$, 4×NH); 17a δ 7.4-7.5 (m, 24H, aromatic-H), 7.0-7.3 (m, 36H, aromatic-H), 3.46 (s, 4H, 2×CH$_2$), 2.44 (m, 8H, 4×CH$_2$N$^{III}$), 2.16 (m, 8H, 4×CH$_2$N$^{II}$), 1.6-1.8 (m, 12H, 4×CH$_2$, 4×NH); 17b δ 7.6 (m, 24H, aromatic-H), 7.05-7.4 (m, 36H, aromatic-H), 3.5 (s, 4H, 2×CH$_2$), 2.3-2.5 (m, 8H, 4×CH$_2$N$^{III}$), 2.15 (m, 8H, 4×CH$_2$N$^{II}$), 1.7 (m, 8H, 2×CH$_2$, 4×NH), 1.45 (m, 8H, 4×CH$_2$).

Synthesis of 18a and 19a Via Tetranitrile Reduction

The diamine (1,2-ethanediamine or 1,3-propanediamine) was dissolved at room temperature in acrylonitrile (50 ml). Glacial acetic acid (40 mmol) was added and the solution was heated at reflux under nitrogen for 24 h. Excess of acrylonitrile was evaporated, the residue was taken up in AcOEt and the solution was washed successively with an aqueous solution of 1 N NaOH and brine, dried over K$_2$CO$_3$ and concentrated to give a yellow oil that was purified by filtration on silica gel using AcOEt as eluent, which yielded a white solid. $^1$H NMR (CDCl$_3$): 7a δ 2.88 (t, 8H, 4×CH$_2$N, J=6.5 Hz), 2.70 (s, 4H, 2×CH$_2$), 2.50 (t, 8H, 4×CH$_2$CN); 8a δ 2.84 (t, 8H, 4×CH$_2$, J=6.6 Hz), 2.64 (t, 4H, 2×CH$_2$, J=6.7 Hz), 2.50 (t, 8H, 4×CH$_2$, J=6.6 Hz), 1.65 (quint, 2H, CH$_2$, J=6.7 Hz).

The nitrile (7a or 8a) (1.2 mmol) (see FIG. 1) was dissolved in anhydrous EtOH (95 ml). A solution of NaOH (1.13 g) in 95% EtOH (30 ml) was added, followed by wet Raney nickel as catalyst. Hydrogenation was performed at 40 psi overnight. The catalyst was filtered off and the solvent was evaporated. The residue was dissolved in water and extracted with CHCl$_3$ three times. The organic portions were combined, dried over K$_2$CO$_3$ and concentrated to give an oil, which was dissolved in 1 N HCl. The water was evaporated and the solid was purified by ion exchange chromatography. ($^1$H NMR (D$_2$O)): 18a δ 3.84 (s, 4H, 2×CH$_2$), 3.46 (m, 8H, 4×CH$_2$N), 3.15 (m, 8H, 4×CH$_2$NH$_2$), 2.23 (m, 8H, 4×CH$_2$); 19a δ 3.40 (m, 12H, 6×CH$_2$N), 3.13 (t, 8H, 4×CH$_2$NH$_2$, J=7.7 Hz), 2.30 (m, 2H, CH$_2$), 2.15-2.25 (m, 8H, 4×CH$_2$). $^{13}$C NMR (D$_2$O): 19a, 52.99 (4×CH$_2$N), 52.70 (2×CH$_2$N), 39.31 (CH$_2$NH$_2$), 24.50 (4×CH$_2$), 21.7 (CH$_2$).

Dimerization Using an Amidation-reduction Pathway

Direct crossalkylation of triamines with saturated alkyl chain linkers led to undesirable cyclization of the terminal protected amine. Thus, compounds 20a-b, 21a-b, 22a-b, 23a-b and 24a-b (see FIG. 1) had to be prepared via amidation of the secondary amino group of spermidine and norspermidine with the appropriate diacyl chloride and reduction reactions. 1a or 1b and triethylamine (1.5 equiv) were dissolved in CHCl$_3$ and the solution was cooled to 0° C. in an ice bath. To this solution was slowly added the desired commercially available diacyl chloride (0.48 equiv). The mixture was then refluxed for 3 hours, washed with water and dried over anhydrous sodium sulfate. After removal of the solvent, a filtration on silica gel pre-treated with triethylamine and eluted with AcOEt gave the pure amides in 80 to 95% yields. $^1$H NMR (CDCl$_3$): 2a δ 7.44 (m, 24H, aromatic-H), 7.1-7.3 (m, 36H, aromatic-H), 3.25-3.35 (m, 8H, 4×CH$_2$N$^{III}$), 2.52 (s, 4H, 2×CH$_2$CO), 2.08 (m, 8H, 4×CH$_2$N$^{II}$), 1.68 (m, 12H, 4×CH$_2$, 4×NH); 2b δ 7.5 (m, 24H, aromatic-H), 7.1-7.3 (m, 36H, aromatic-H), 3.1-3.4 (m, 8H, 4×CH$_2$N$^{III}$), 2.4-2.6 (m, 4H, 2×CH$_2$CO), 2.1 (m, 8H, CH$_2$N$^{II}$), 1.7 (m, 4H, 2×CH$_2$), 1.4-1.6 (m, 12H, 4×CH$_2$, 4×NH); 3a δ 7.52 (m, 24H, aromatic-H), 7.12-7.38 (m, 36H, aromatic-H), 3.30 (m, 4H, 2×CONCH$_2$), 3.12 (m, 4H, 2×CONCH$_2$), 2.26 (m, 4H, 2×CH$_2$N$^{II}$), 2.16 (m, 4H, 2×CH$_2$N$^{II}$), 2.06 (m, 4H, 2×CH$_2$CO), 1.60-1.98 (m, 14H, 5×CH$_2$, 4×NH); 3b δ 7.4 (m, 24H, aromatic-H), 7.0-7.2 (m, 36H, aromatic-H), 2.9-3.3 (m, 8H, CH$_2$N$^{III}$), 2.1-2.3 (m, 4H, 2×CH$_2$CO), 2.0 (m, 8H, 4×CH$_2$N$^{II}$), 1.6 (m, 4H, 2×CH$_2$), 1.2-1.4 (m, 14H, 5×CH$_2$, 4×NH); 4a δ 7.48 (m, 24H, aromatic-H), 7.1-7.4 (m, 36H, aromatic-H), 3.38 (m, 4H, 2×CONCH$_2$), 3.10 (m, 4H, 2×CONCH$_2$), 2.22 (m, 4H, 2×CH$_2$CO), 2.12 (m, 4H, 2×CH$_2$N$^{II}$), 1.70 (m, 6H, 3×CH$_2$), 1.56 (m, 4H, 4×NH); 4b δ 7.5 (m, 24H, aromatic-H), 7.15-7.35 (m, 36H, aromatic-H), 3.1-3.5 (m, 8H, 4×CH$_2$N$^{III}$), 2.05-2.35 (m, 12H, 2×CH$_2$CO, 4×CH$_2$N$^{II}$), 1.4-1.8 (m, 20H, 8×CH$_2$, 4×NH); 5a δ 7.4-7.5 (m, 24H, aromatic-H), 7.1-7.3 (m, 36H, aromatic-H), 3.39 (m, 4H, 2×CONCH$_2$), 3.21 (m, 4H, 2×CONCH$_2$), 2.1-2.3 (m, 12H, 6×CH$_2$), 1.5-1.9 (m, 16H, 6×CH$_2$, 4×NH), 1.34 (m, 4H, 2×CH$_2$); 5b δ 7.65 (m, 24H, aromatic-H), 7.5-7.2 (m, 36H, aromatic-H), 3.1-3.6 (m, 8H, 4×CH$_2$N), 2.4 (m, 4H, 2×CH$_2$CO), 2.3 (m, 8H, 4×CH$_2$N$^{II}$), 1.45-1.9 (m, 24H, 10×CH$_2$, 4×NH); 6a δ 7.5-7.6 (m, 24H, aromatic-H), 7.1-7.4 (m, 36H, aromatic-H), 3.50 (m, 4H, 2×CH$_2$NCO), 3.29 (m, 4H, 2×CH$_2$NCO), 2.1-2.3 (m, 12H, 6×CH$_2$), 1.6-2.0 (20H, 8×CH$_2$, 4×NH), 1.47 (br s, 4H, 2×CH$_2$); 6b δ 7.4 (m, 24H, aromatic-H), 7.1-7.3 (m, 36H, aromatic-H), 3-3.45 (m, 8H, 4×CH$_2$N$^{III}$), 2.2 (m, 4H, 2×CH$_2$CO), 2.1 (m, 8H, 4×CH$_2$N$^{II}$), 1.2-1.75 (m, 28H, 12×CH$_2$, 4×NH).

The amide was added to a suspension of LiAlH$_4$ (10 equiv) in dry tetrahydrofuran. The mixture was refluxed under nitrogen for 3 d or until it was of a deep red color. The reaction mixture was allowed to attain room temperature, CHCl$_3$ was added, and excess hydride were hydrolyzed by dropwise addition of H$_2$O, followed by a 15% (w/v) NaOH solution in H$_2$O. Vigorous stirring was maintained for 20 minutes, the solid was filtered off under suction and washed thoroughly with CHCl$_3$. After evaporation, the residue was purified by flash column chromatography with AcOEt/petroleum ether (1:1) as eluent, affording the pure compounds. Yields varied from 35 to 85%. $^1$H NMR (CDCl$_3$): 9a δ 7.4-7.5 (m, 24H, aromatic-H), 7.1-7.3 (m, 36H, aromatic-H), 2.41 (m, 8H, 4×CH$_2$N$^{III}$), 2.35 (m, 4H, 2×CH$_2$N$^{III}$), 2.15 (m, 8H, 4×CH$_2$N$^{II}$), 1.81 (br s, 4H, 4×NH), 1.61 (m, 8H, 4×CH$_2$), 1.29 (m, 4H, 2×CH$_2$); 9b δ 7.75 (m, 24H, aromatic-H), 7.25-7.5 (m, 36H, aromatic-H), 2.55 (m, 12H, 6×CH$_2$N$^{III}$), 2.35 (m, 8H, 4×CH$_2$N$^{II}$), 1.8 (m, 4H, 2×CH$_2$), 1.45-1.7 (m, 18H, 7×CH$_2$, 4×NH); 10a δ 7.4-7.5 (m, 24H, aromatic-H), 7.1-7.3 (m, 36H, aromatic-H), 2.41 (m, 8H, 4×CH$_2$N$^{III}$), 2.32 (m, 4H, 2×CH$_2$N$^{III}$), 2.14 (m, 8H, 4×CH$_2$N$^{II}$), 1.80 (br s, 4H, 4×NH), 1.60 (m, 8H, 4×CH$_2$), 1.34 (m, 4H, 2×CH$_2$), 1.15 (m, 2H, CH$_2$); 10b 6.7.55 (m, 24H, aromatic-H), 7.15-7.35 (m, 36H, aromatic-H), 2.4-2.6 (m, 12H, 6×CH$_2$N$^{III}$), 2.2 (m, 8H, 4×CH$_2$N$^{II}$), 1.7 (m, 4H, 2×CH$_2$), 1.4-1.6 (m, 18H, 7×CH$_2$', 4×NH); 11a δ 7.5 (m, 24H, aromatic-H), 7.1-7.3 (m, 36H, aromatic-H), 2.3-2.5 (m, 12H, 6×CH$_2$N$^{III}$), 2.15 (m, 8H, 4×CH$_2$N$^{II}$), 1.84 (br s, 4H, 4×NH), 1.62 (m, 8H, 4×CH$_2$), 1.35 (m, 4H, 2×CH$_2$), 1.22 (m, 4H, 2×CH$_2$); 11b δ 7.5 (m, 24H, aromatic-H), 7.1-7.4 (m, 36H, aromatic-H), 2.3-2.45 (m, 12H, 6×CH$_2$N$^{III}$), 2.1 (m, 8H, CH$_2$N$^{II}$), 1.6 (m, 4H, 2×CH$_2$), 1.2-1.5 (m, 16H, 8×CH$_2$); 12a δ 7.4-7.5 (m, 24H, aromatic-H), 7.1-7.3 (m, 36H, aromatic-H), 2.41 (m, 8H, 4×CH$_2$N$^{III}$), 2.34 (m, 4H, 2×CH$_2$N$^{III}$), 2.12 (t, 8H, 4×CH$_2$N$^{11}$, J=6.5 Hz), 1.77 (br s, 4H, 4×NH), 1.58 (m, 8H, 4×CH$_2$), 1.34 (m, 4H, 2×CH$_2$), 1.23 (m, 8H, 4×CH$_2$); 12b δ 7.6 (m, 24H, aromatic-H), 7.2-7.4 (m, 36H, aromatic-H), 2.4-2.55 (m, 12H, 6×CH$_2$N$^{III}$), 2.2 (m, 8H, 4×CH$_2$N$^{II}$), 1.7 (m, 4H, 2×CH$_2$), 1.2-1.55 (m, 20H, 10×CH$_2$); 13a δ 7.4-7.5 (m, 24H, aromatic-H) and 7.1-7.3 (m, 36H, aromatic-H), 2.45 (m, 8H, 4×CH$_2$N$^{III}$), 2.39 (m, 4H, 2×CH$_2$N$^{III}$), 2.17 (t, 8H, 4×CH$_2$N$^{II}$, J=6.5 Hz), 1.83 (br s, 4H, 4×NH), 1.62 (m, 8H, 4×CH$_2$), 1.1-1.3 (m, 16H, 8×CH$_2$); 13b δ 7.6 (m, 24H, aromatic-H) 7.2-7.4 (m, 36H, aromatic-H), 2.35-2.55 (m, 12H, 6×CH$_2$N$^{III}$), 2.2 (m, 8H, 4×CH$_2$N$^{II}$), 1.7 (m, 4H, 2×CH$_2$), 1.2-1.55 (m, 24H, 12×CH$_2$).

Deprotection of the Primary Amines

For all compounds except 18a and 19a (see FIG. 1), the final step of the synthesis involved removal of the protecting trityl group. The pure tritylated dimeric compound was taken up in 3 M HCl and refluxed for 4 h. The mixture was then filtered, the filtrate washed with ether and the aqueous solution was concentrated to dryness. At this step, the yield of the deprotection was 90-95%. If necessary, a further purification was accomplished by cation exchange chromatography using Dowex 50W-X8. The hexahydrochloride form of the expected compound was eluted with HCl within the range of 5 to 6 M. $^1$H NMR (D$_2$O): 18a δ 3.84 (s, 4H, 2×CH$_2$N$^{III}$), 3.46 (m, 8H, 4×CH$_2$N), 3.15 (m, 8H, 4×CH$_2$N), 2.23 (m, 8H, 4×CH$_2$); 18b: δ 3.75 (m, 4H, 2×CH$_2$N$^{III}$), 3.35 (t, 8H, 4×CH$_2$N), 3.0 (m, 8H, 4×CH$_2$N), 2.1 (m, 4H, 2×CH$_2$), 1.6-1.9 (m, 8H, 4×CH$_2$); 19a: $^1$H NMR (D$_2$O) δ 3.40 (m, 12H, 6×CH$_2$N$^{III}$), 3.13 (t, 8H, 4×CH$_2$N$^I$, J=7.7 Hz), 2.30 (m, 2H, CH$_2$), 2.15-2.25 (m, 8H, 4×CH$_2$); 19b: δ 3.25 (m, 12H, 6×CH$_2$N$^{III}$), 3.0 (m, 8H, 4×CH$_2$N$^I$), 2.2 and 2.1 (2m, 6H, 3×CH$_2$), 1.6-1.9 (m, 8H, 4×CH$_2$); 20a: δ 3.28-3.34 (m, 12H, 6×CH$_2$N), 3.08 (t, 8H, 4CH$_2$NH$_2$, J=7.7 Hz), 2.1-2.2 (m, 8H, 4×CH$_2$), 1.82 (m, 4H, 2×CH$_2$); 20b: δ 3.25 (m, 12H, 6×CH$_2$N$^{III}$), 3.0 (m, 8H, 4×CH$_2$N$^I$), 2.1 (m, 4H, 2×CH$_2$), 1.7 (m, 12H, 6×CH$_2$); 21a: δ 3.25 (m, 8H, 4×CH$_2$N$^{III}$), 3.20 (m, 4H, 2×CH$_2$N$^{III}$), 3.04 (t, 8H, 4×CH$_2$N$^I$, J=7.7 Hz), 2.00-2.15 (m, 8H, 4×CH$_2$), 1.73 (m, 4H, 2×CH$_2$), 1.40 (m, 2H, CH$_2$); 21b: δ 3.2 (m, 12H, 6×CH$_2$N$^{III}$), 3.0 (m, 8H, 4×CH$_2$NH$^I$), 2.1 (m, 4H, 2×CH$_2$), 1.6-1.8 (m, 12H, 6×CH$_2$), 1.35 (m, 2H, CH$_2$); 22a: δ 3.30 (m, 0.8H, 4×CH$_2$N), 3.22 (m, 4H, 2×CH$_2$N), 3.08 (t, 8H, 4×CH$_2$N$^I$, J=7.7 Hz), 2.05-2.20 (m, 8H, 4×CH$_2$), 1.73 (m, 4H, 2×CH$_2$), 1.41 (m, 4H, 2×CH$_2$); 22b: δ 3.2 (m, 12H, 6×CH$_2$N$^{III}$), 3.0 (m, 8H, 4×CH$_2$N$^I$), 2.1 (m, 4H, 2×CH$_2$), 1.6-1.85 (m, 12H, 6×CH$_2$), 1.35 (m, 4H, 2×CH$_2$); 23a: δ 3.26 (m, 8H, 4×CH$_2$N), 3.18 (m, 4H, 2×CH$_2$N), 3.05 (t, 8H, 4×CH$_2$NH$_2$, J=7.7 Hz), 2.1 (m, 8H, 4×CH$_2$), 1.67 (m, 4H, 2×CH$_2$), 1.31 (br s, 8H, 4×CH$_2$); 23b: δ 3.15 (m, 12H, 6×CH$_2$N$^{III}$), 3.0 (m, 8H, 4×CH$_2$N$^I$), 2.05 (m, 4H, 2×CH$_2$), 1.55-1.8 (m, 12H, 6×CH$_2$), 1.3 (s, 8H, 4×CH$_2$); 24a: δ 3.26 (m, 8H, 4×CH$_2$N), 3.17 (m, 4H, 2×CH$_2$N), 3.05 (t, 8H, 4×CH$_2$NH$_2$, J=7.7 Hz), 2.0-2.1 (m, 8H, 4×CH$_2$), 1.66 (m, 4H, 2×CH$_2$), 1.27 (m, 12H, 6×CH$_2$); 24b: δ 3.3 (m, 12H, 6×CH$_2$N$^{III}$), 3.0 (m, 8H, 4×CH$_2$N$^I$), 2.1 (m, 4H, 2×CH$_2$), 1.6-1.85 (m, 12H, 6×CH$_2$), 1.3 (m, 12H, 6×CH$_2$); 25a: δ 6.25 (br s, 2H, CH=CH), 4.02 (br s, 4H, 2×CH$_2$N$^{III}$), 3.28 (m, 8H, 4×CH$_2$N$^{III}$), 3.08 (m, 8H, 4×CH$_2$N$^I$), 2.1-2.2 (m, 8H, 4×CH$_2$); 25b: δ 6.2 (m, 2H, CH=CH), 4.0 (m, 4H, 2×CH$_2$N$^{III}$), 3.3 (m, 8H, 4×CH$_2$N$^{III}$), 3.0 (m, 8H, 4×CH$_2$N$^I$), 2.1 (m, 4H, 2×CH$_2$N$^I$), 1.6-1.9 (m, 8H, 4×CH$_2$); 26a: δ 43.2 (s, 4H, 2×CH$_2$N$^I$), 3.39 (m, 8H, 4×CH$_2$N$^{III}$), 3.07 (t, 8H, 4×CH$_2$N$^I$, J=7.7 Hz), 2.1 (m, 8H, 4×CH$_2$); 26b: δ 4.2 (m, 4H, 2×CH$_2$N$^{III}$), 3.35 (m, 8H, 4×CH$_2$N$^{III}$), 3.0 (m, 8H, 4×CH$_2$N$^I$), 2.1 (m, 4H, 2×CH$_2$N$^I$), 1.6-1.9 (m, 8H, 4×CH$_2$N$^I$); 27a: δ 7.6-7.8 (m, 4H, aromatic-H), 4.54 (s, 4H, 2×CH$_2$Ph) 3.33 (t, 8H, 4×CH$_2$N$^{III}$, J=8.4 Hz), 3.07 (t, 8H, 4×CH$_2$N$^I$, J=7.7 Hz), 2.20 (m, 8H, 4×CH$_2$); 27b: δ 7.65 (2s, 4H, aromatic-H), 4.45 (s, 4H, 2×CH$_2$Ph) 3.25 (m, 8H, 4×CH$_2$N$^{III}$), 3.0 (m, 8H, 4×CH$_2$N$^I$), 2.1 (m, 4H, 2×CH$_2$), 1.6-1.9 (m, 8H, 4×CH$_2$); 28a: δ 7.64 (m, 4H, aromatic-H), 4.50 (s, 4H, 2×CH$_2$Ph), 3.29 (m, 8H, 4×CH$_2$N$^{III}$), 3.04 (t, 8H, 4×CH$_2$N$^I$), 2.18 (m, 8H, 4×CH$_2$); 28b: δ 7.65 (s, 4H, aromatic-H), 4.4 (s, 4H, 2×CH$_2$Ph), 3.2 (m, 8H, 4×CH$_2$N$^{III}$), 2.95 (m, 8H, 4×CH$_2$N$^I$), 2.1 (m, 4H, 2×CH$_2$), 1.5-1.9 (m, 8H, 4×CH$_2$). $^{13}$C NMR (D$_2$O): 19a 4×CH$_2$N, 52.99, 2×CH$_2$N, 52.70, CH$_2$NH$_2$: 39.31, 4×CH$_2$: 24.50, 2×CH$_2$: 21.7; 19b CH$_2$N: 55.30, 52.79, 52.66, CH$_2$NH$_2$: 41.58, 39.27, CH$_2$CH$_2$: 26.68, 24.46, 23.36, 21.71.

Cell Culture

All cell lines were obtained from the American Type Culture Collection (Rockville, Md.). T-47D, ZR-75-1 and MDA-MB-231 human breast cancer cells were maintained in RPMI 1640 medium supplemented as described (U.S. Pat. No. 6,083,496), except that 17 β-estradiol was omitted for the latter cell line. MCF-7 breast cancer cells were grown in Dulbecco's Minimal Essential Medium supplemented with 10% FBS (v/v), 2 mM L-glutamine, 1 nM 17 β-estradiol and antibiotics. L1210 mouse leukemia cells were routinely grown in RPMI 1640 medium as described (Poulin et al. (1995) *Biochem. J.* 312, 749-756). Jurkat human leukemia cells and LAN-1 human neuroblastoma cells were maintained in RPMI 1640 medium supplemented with 10% heat-inactivated FBS (v/v), 2 mM L-glutamine and antibiotics.

Chinese hamster ovary cells (CHO-K1, CHO-TOR and CHO-MG) were routinely grown in α-Minimal Essential Medium (alpha modification) supplemented with Cosmic™ calf serum as described (Torossian et al. (1996) *Biochem. J.* 319, 21-26) experimental media used for CHO cells were supplemented with dextran-coated charcoal-treated FBS since Cosmic™ calf serum was found to contain traces of polyamines. All cell lines were incubated in a water-saturated 5% $CO_2$ at 37° C.

Determination of Polyamine Uptake Activity

The rate of diamine and polyamine transport was determined in T-47D and ZR-75-1 cells incubated in serum-free RPMI 1640 medium as previously described (U.S. Pat. No. 6,083,496; Covassin et al. (1999) *Bioorg. Med. Chem. Lett.* 9, 1709-1714), using 20 µM [$^3$H]putrescine (179 Ci/mol), 5 µM [$^3$H]spermidine (246 Ci/mol) and 3 µM [$^{14}$C]spermine (300-400 mCi/mol) respectively, as substrates for a 20-min assay period. Uptake activity was expressed per amount of DNA as fluorometrically determined using 3,5-diaminobenzoic acid (Simard et al. (1990) *Endocrinology* 126, 3223-3231). Kinetic parameters of polyamine transport inhibition for the transport antagonists were determined by Lineweaver-Burke analysis of uptake activity in the presence of 0.1 µM [$^3$H] putrescine, 0.03 µM [$^3$H]spermidine, and 0.01 µM [$^{14}$C]spermine plus increasing concentrations of nonradioactive substrate. For competitive inhibitors, $K_i$ values were estimated by iterative curve fitting for sigmoidal equations describing transport rates in the presence of increasing concentrations of antagonist, using the Cheng-Prusoff equation for competitive inhibition (U.S. Pat. No. 6,083,496). Lineweaver-Burke analysis showed that all transport antagonists were pure competitive inhibitors of diamine and polyamine uptake, and $K_i$ values calculated according to the Cheng-Prusoff equation were in good agreement with those derived from the former analysis.

Effect of Inhibitors on Cell Proliferation

The effect of transport inhibitors on cell proliferation was evaluated by determination of cell number (L1210, Jurkat) using electronic sizing with a Model ZM Coulter counter (Coulter Electronics, Hialeah, Fla.), or DNA content per culture (for all other cell lines) with the 3,5-diaminobenzoic acid assay. The respective cell culture medium for each cell line was supplemented with increasing concentrations of inhibitors (0.01-300 µM), in the presence or absence of 1 mM aminoguanidine as an inhibitor of bovine serum amine oxidase (BSAO) (U.S. Pat. No. 6,083,496). Cytotoxicity of the inhibitors was determined in the presence or absence of aminoguanidine, and was confirmed by a trypan blue exclusion assay.

To determine the ability of polyamine transport antagonists to potentiate DFMO-induced inhibition of cell proliferation in the presence of exogenous polyamines, cells were grown for the indicated period in growth medium supplemented with 1 mM aminoguanidine, and either DFMO (1 to 5 mM), the indicated transport inhibitor (50 or 100 µM), or the combination thereof, as well as increasing concentrations of spermidine (0.1 to 300 µM). Fresh medium was added every other day, and cell mass was determined at various time points during the period of exponential growth, or at the end of the experimental period. For the latter experiments, the FBS supplement was replaced with dextran-coated charcoal-treated FBS (5%, v/v) plus 0.5 µg/ml insulin in the case of T-47D, ZR-75-1 and MCF-7 cells (U.S. Pat. No. 6,083,496).

Determination of Intracellular Polyamine and Analogue Contents

To determine the effect of the polyamine transport antagonists on intracellular polyamine contents, CHO-K1 cells were plated in 100-mm culture dishes at $1 \times 10^5$ cells/dish, and 24 h later, fresh medium containing 1 mM aminoguanidine and the indicated transport antagonist (100 µM), in the presence or absence of 5 mM DFMO. At the indicated time intervals, medium was removed, cell monolayers were rinsed twice: with 10 ml of ice-cold $Ca^{2+}/Mg^{2+}$-free phosphate-buffered saline (PBS) (2.7 mM KCl, 1.5 mM $KH_2PO_4$, 8.1 mM $Na_2HPO_4$, 137 mM NaCl), and cells were harvested by low-speed centrifugation (2400 g for 5 min at 4° C.). Cell pellets were resuspended in 200 µl of 10% (v/v) trichloroacetic acid and store at −20° C. until further analysis. Polyamine content was then determined by ion-pair reverse phase HPLC with fluorometric detection after post-column derivatization with o-phthaldialdehyde as described (U.S. Pat. No. 6,083,496). Polyamine contents are expressed as nmol per mg of total cell proteins as determined by colorimetric determination of protein in the trichloroacetic acid-insoluble pellet after solubilization with 200 µl of 1 N NaOH, using bovine serum albumin (fraction V) as standard (U.S. Pat. No. 6,083,496).

Animal Experiments

Four to five-week-old female intact CD-1® mice and immunodeficient (nude) CD-1 mice were purchased from Charles River Laboratories (Wilmington, Mass.). Animals were housed at 2 or 3 individuals per cage. Nude mice were housed in filtered laminar air flow hoods with air filter tops. Cages, bedding, and food used for nude mouse experiments' were autoclaved before use. Water and drink solutions of DFMO and BNSD-X were filter sterilized prior to use.

To determine the bioavailability of BNSD-X, escalating doses of BNSD-X were dissolved in the drinking water (0, 0.25, 0.5, 1, 2 and 4%, w/v) and were made available to CD-1 mice (n=6/group) ad libitum. Animals were sacrificed after 96 h, and blood was immediately collected to determine the concentration of BNSD-X and polyamines in plasma and erythrocytes by HPLC using the dansylation method (Kabra et al. (1986) *J. Chromatogr.* 380:19-32).

To assess the relative toxicity of BNSD-X, the drug was administered as a 1% (w/v) solution in the drinking water to CD-1 mice with ad libitum access for 14 d. Mice were weighed every other day during the experiment. At the end of the experiment, mice were sacrificed, and organs (kidneys, liver, and spleen) were immediately weighed. Organs were then saved in 10% formalin for morphological examination by an in-house pathologist at the CHUL Research Center (Quebec City, Canada). Acute and subacute oral toxicity of BNSD-X was also separately determined by administering the drug by gavage (0-5 g/kg body weight).

For human xenograft experiments, athymic CD-1 mice were inoculated with $5 \times 10^6$ MDA-MB-231 human breast cancer cells (grown in tissue culture incubators to mid-exponential phase) in both sides of the inguinal mammary fat pad. After ~2 weeks, when the tumor had reached a diameter ~4 mm (as measured with a caliper), control mice were paired to treated ones in accordance with tumor volume (time zero). Animals were allowed free access to water containing 0, 0.3 or 1% DFMO (w/v), plus or minus 1% (w/v) BNSD-X (7 mice/experimental group). Tumor volume (V) was measured twice weekly with a caliper in 2 dimensions using the approximation $V=(L \times w^2)/2$, where L is the length and w is the width of the xenograft (Bandyopadhyay et al., (2002)

Cancer Res. 62:4690-4695). Animals were sacrificed after 39 d (i.e. when tumor size in control mice had reached about 500 mm$^3$). Mammary tumors were be excised and weighed.

Results

Design and Synthesis of Dimeric Spermidine and Norspermidine Derivatives

Applicants have recently shown that dimerization of spermidine or sym-norspermidine through cross-alkylation of the central amino nitrogen of the polyamine backbone with an aliphatic or aromatic side chain leads to competitive antagonists of diamine and polyamine transport (Covassin et al. (1999) *Bioorg. Med. Chem. Lett.* 9, 1709-1714). Some of the polyamine derivatives from the series exhibited a much higher potency than DESC, which was previously described as a cell-impermeant transport inhibitor with the general design of a spermine dimer (U.S. Pat. No. 6,083,496). In order to further understand the structure-function relationships underlying transport inhibition by these novel polyamine analogs, and to characterize their biological properties, we synthesized a more extensive series of spermidine and norspermidine dimers with a similar design (therefrom referred to as BSD and BNSD compounds, respectively) (FIG. 1).

The ability of BSD and BNSD compounds to inhibit uptake of the main natural substrates of the mammalian polyamine carrier, namely putrescine, spermidine and spermine, was evaluated using T-47D human breast cancer cells (Table 1).

Data are presented as the mean±SD of at least two independent determinations of IC$_{50}$ values, each based on triplicate determinations of uptake velocity at increasing inhibitor concentrations.

All dimers tested behaved as competitive inhibitors as shown by Lineweaver-Burke analysis (not shown). The relative potency of transport inhibition by the hexamines was greater for putrescine than for either spermidine or spermine as substrates, as expected from the observation that the K$_i$ values of spermidine and spermine toward putrescine transport are lower than the K$_m$ of putrescine in mammalian cells (Lessard et al. (1995) *J. Biol. Chem.* 270, 1685-1694; U.S. Pat. No. 6,083,496); Seiler et al. (1990) *Int. J. Biochem.* 22, 211-218). All new dimeric compounds behaved as stronger inhibitors of diamine and polyamine uptake than DESC, a previously described spermine dimer and transport antagonist (Seiler et al. (1990) *Int. J. Biochem.* 22, 211-218), except for spermidine and norspermidine derivatives with a C4 butyne linker (26a and 26b) or BNSD-2 (18a), the norspermidine derivative bearing the shortest linker tested. The ability of BNSD derivatives to inhibit either spermidine and spermine uptake clearly increased with the aliphatic linker chain length, with two optima observed for the n-hexyl and n-decyl crosslinkers (Table 1 and FIG. 2A). In contrast, spermidine dimers with crosslinkers bearing from 2 to 10 methylene groups inhibited spermidine transport with comparable potency, whereas the potency of spermine transport inhibition by these compounds increased with linker chain length for crosslinkers bearing more than 4 methylene groups. Interestingly, while BSD compounds with short crosslinkers (≦3 to

TABLE 1

Relative potency of dimeric spermidine and norspermidine derivatives as inhibitors of diamine and polyamine transport in T-47D breast cancer cells

| Inhibitor (acronym) | Linker | K$_m$ or K$_i$ (μM) | | |
|---|---|---|---|---|
| | | [$^3$H]Putrescine | [$^3$H]Spermidine | [$^{14}$C]Spermine |
| Putrescine | | 7.4 ± 1.1 | ND$^a$ | ND |
| Spermidine | | ND | 4.4 ± 0.9 | ND |
| Spermine | | 0.65 ± 0.12 | 0.92 ± 0.08 | 2.7 ± 0.4 |
| DESC | | 3.1 ± 0.4 | 12.6 ± 1.4 | 15.9 ± 4.0 |
| Saturated linkers | | | | |
| 18a (BNSD-2) | (CH$_2$)$_2$ | 1.2 ± 0.2 | 17.3 ± 1.4 | 20.4 ± 6.9 |
| 18b (BSD-2) | (CH$_2$)$_2$ | 0.65 ± 0.07 | 3.0 ± 0.5 | 5.9 ± 1.1 |
| 19a (BNSD-3) | (CH$_2$)$_3$ | 1.6 ± 0.4 | 8.3 ± 0.8 | 6.2 ± 1.7 |
| 19b (BSD-3) | (CH$_2$)$_3$ | 0.24 ± 0.03 | 1.7 ± 0.4 | 2.8 ± 0.6 |
| 20a (BNSD-4) | (CH$_2$)$_4$ | 0.72 ± 0.20 | 4.9 ± 0.1 | 4.3 ± 0.7 |
| 20b (BSD-4) | (CH$_2$)$_4$ | 0.52 ± 0.06 | 2.4 ± 0.4 | 6.2 ± 0.6 |
| 21a (BNSD-5) | (CH$_2$)$_5$ | 0.54 ± 0.11 | 3.1 ± 0.5 | 2.6 ± 0.7 |
| 21b (BSD-5) | (CH$_2$)$_5$ | 0.57 ± 0.10 | 0.83 ± 0.08 | 8.0 ± 1.1 |
| 22a (BNSD-6) | (CH$_2$)$_6$ | 0.72 ± 0.18 | 2.4 ± 0.3 | 0.82 ± 0.10 |
| 22b (BSD-6) | (CH$_2$)$_6$ | 0.91 ± 0.11 | 0.69 ± 0.16 | 6.3 ± 0.8 |
| 23a (BNSD-8) | (CH$_2$)$_8$ | 0.66 ± 0.06 | 7.5 ± 1.6 | 7.0 ± 1.0 |
| 23b (BSD-8) | (CH$_2$)$_8$ | 0.44 ± 0.07 | 3.0 ± 0.2 | 3.6 ± 0.7 |
| 24a (BNSD-10) | (CH$_2$)$_{10}$ | 1.6 ± 0.4 | 1.5 ± 0.2 | 2.4 ± 0.7 |
| 24b (BSD-10) | (CH$_2$)$_{10}$ | 0.14 ± 0.01 | 1.2 ± 0.2 | 1.9 ± 0.3 |
| Unsaturated | | | | |
| 25a (BNSD-4-ene) | CH$_2$CH=CHCH$_2$ | 0.10 ± 0.01 | 1.8 ± 0.1 | 1.5 ± 0.1 |
| 25b (BSD-4-ene) | CH$_2$CH=CHCH$_2$ | 0.27 ± 0.04 | 2.0 ± 0.5 | 1.6 ± 0.2 |
| 26a (BNSD-4-yne) | CH$_2$C≡CCH$_2$ | 2.6 ± 0.4 | 25.6 ± 4.0 | 12.8 ± 2.2 |
| 26b (BSD-4-yne) | CH$_2$C≡CCH$_2$ | 1.9 ± 0.4 | 16.9 ± 2.0 | 27.7 ± 3.2 |
| 27a (BNSD-X$_m$) | CH-Ph-CH (meta) | 0.64 ± 0.08 | 3.0 ± 0.5 | 5.7 ± 1.3 |
| 27b (BSD-X$_m$) | CH-Ph-CH (meta) | 0.19 ± 0.05 | 1.6 ± 0.1 | 2.4 ± 0.3 |
| 28a (BNSD-X) | CH-Ph-CH (para) | 0.16 ± 0.03 | 1.5 ± 0.1 | 1.5 ± 0.1 |
| 28b (BSD-X) | CH-Ph-CH (para) | 0.28 ± 0.02 | 2.0 ± 0.2 | 2.9 ± 0.6 |

4 methylene groups) were stronger inhibitors of either spermidine or spermine uptake, BNSD-5 and BNSD-6 were more potent antagonists of spermine transport than the corresponding BSD compounds (Table 1 and FIGS. 2A and 2B). Spermidine and norspermidine dimers with either a trans-but-2-ene (BSD-4-ene, BNSD-4-ene) or p-xylene crosslinker (BSD-X, BNSD-X) were those exhibiting the lowest $K_i$ values against the uptake of all three natural substrates of the polyamine transport system, along with those bearing very long linkers (BNSD-10 and BSD-10). It is noteworthy that the m-xylene tether was less favorable for transport inhibition potency than the p-xylene substitution for the norspermidine, but not the spermidine dimer (Table 1).

Thus, dimerization of spermidine and norspermidine through an aliphatic or aromatic crosslinker tethered to the central nitrogen atom of the polyamine backbone leads to strong antagonists of polyamine transport, with the most potent compounds (e.g. those with a trans-4-ene, a p-xylene or a n-decyl crosslinker) exhibiting $K_i$ values lower than the respective $K_m$ for uptake of the natural substrates of the polyamine carrier. The length and nature of the crosslinker clearly influences the affinity of the resulting dimer for the polyamine transporter in a complex fashion. However, current knowledge on the structural features determining an optimal interaction with the carrier (Li et al. (1997) *Cancer Res.* 57, 234-239; Lessard et al. (1995) *J. Biol. Chem.* 270, 1685-1694) does not easily predict the relative potency observed for the present compounds as inhibitors of polyamine uptake.

Effect of BSD and BNSD Derivatives on Cell Proliferation

Figure 3B:
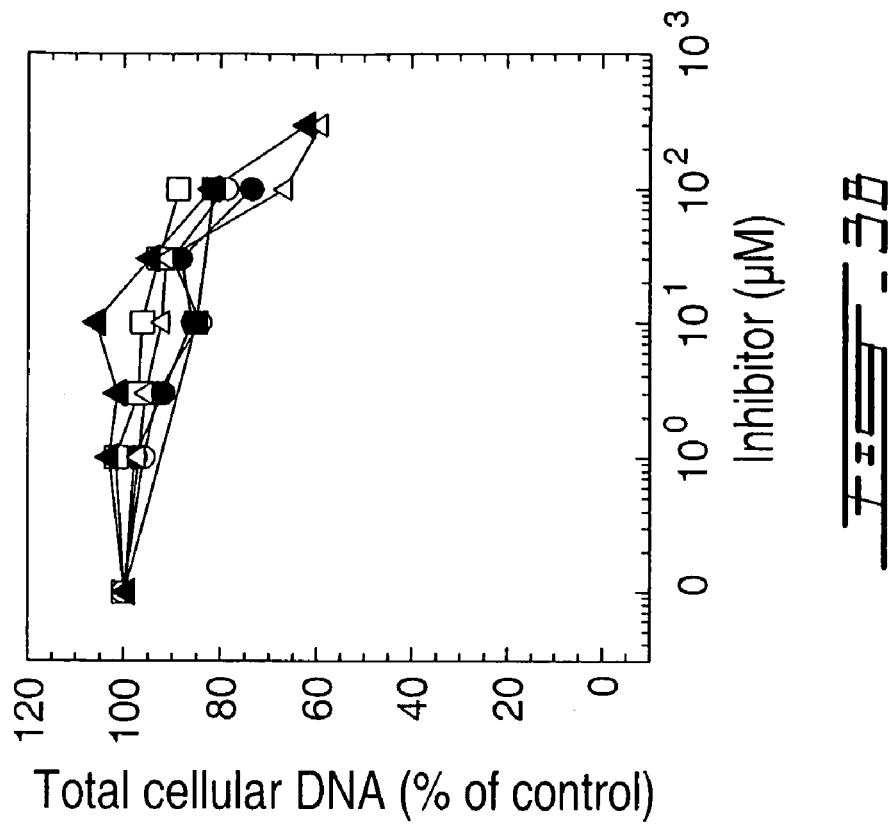
FIGS. 3A and 3B are graphs showing the effect compounds used in a method according preferred embodiment of the present invention, on cell proliferation. In particular, they relate to the effect of selected BSD and BNSD derivatives on T-47D cell proliferation. Cells were incubated for 9 d with the indicated concentrations of BSD-2 (○), BNSD-4 (●), BSD-4 (□), BNSD-6 (■), BSD-10 (Δ), BSD-4-ene (▲) and BSD-4-yne (▼) in medium containing 1 mM aminoguanidine, and total DNA content per culture was then determined. B, Effect of BNSD-X (N,N,N',N'-tetrakis-(3-aminopropyl)-p-diaminoxylene) on cell proliferation in various mammalian cell lines. Jurkat (○), LAN-1 (●), L1210 (□), T-47D (■), ZR-75-1 (Δ) and MDA-MB-231 (▲) cells were grown to near confluency or saturation (for 4 to 11 d according to the cell line considered) with the indicated concentrations of BNSD-X in the presence of 1 mM aminoguanidine, and total DNA content per culture was then determined. Data are given as the mean±SD for triplicate cultures from one out of at least two identical experiments.
Figure 3A:
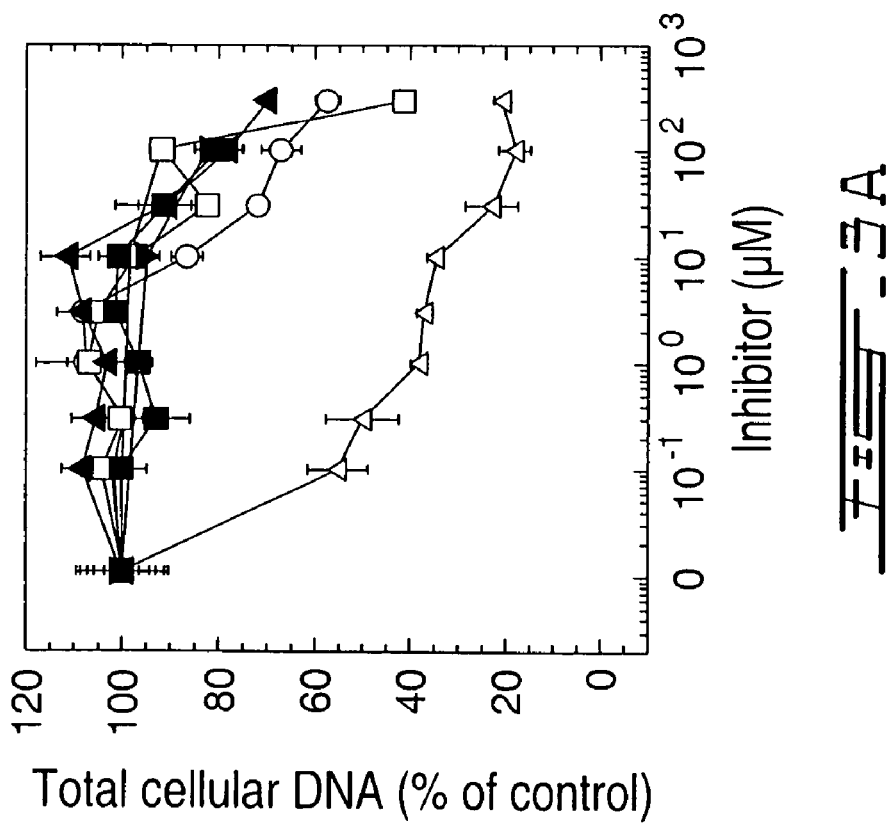

In order to determine whether the BSD and BNSD derivatives were suitable as non-cytotoxic inhibitors of polyamine transport, their effect on cell proliferation was assessed in the T-47D (FIG. 3A) and MCF-7 (not shown) human breast cancer cell lines. For these experiments, aminoguanidine was added to the medium to inhibit BSAO activity (see below). Most of the novel series of triamine dimers had little effect on cell proliferation at concentrations up to 30-100 µM. Exceptions found were dimers with the shortest (BSD-2, BNSD-2, BSD-3 and BNSD-3) or longest aliphatic crosslinkers (BNSD-10, BSD-10) (FIG. 3A and data not shown), the latter being markedly cytotoxic at concentrations as low as 0.1 µM. N,N,N',N'-tetrakis-(3-aminopropyl)-p-diaminoxylene (BNSD-X), the antagonist that exhibited the most favorable properties as a polyamine transport inhibitor (cf. below), was remarkably inert toward a panel of mammalian cell lines of various species and/or tissue origins (FIG. 3B).

Polyamines with free aminopropyl ends are potential substrates for oxidative deamination by copper/topa quinone-containing BSAO with the resulting formation of cytotoxic hydrogen peroxide and aminoaldehydes as by-products. Applicants thus assessed the effect of aminoguanidine, an inhibitor of BSAO (Lee et al. (1998) *J Biol Chem.* 273:19490-19494), on the toxicity of selected triamine dimers toward T-47D cells (FIGS. 4A and 4B). Interestingly, BNSD-3 and BNSD-X were considerably more cytotoxic than their spermidine-like homologs in the absence of aminoguanidine. On the other hand, aminoguanidine addition abolished most of the cytotoxicity due to the addition of BNSD-3, BNSD-X and BSD-X, suggesting that BSAO activity is responsible for the lethal effects observed for these dimers. These results clearly suggest that the presence of four symmetrically arranged aminopropyl groups is a critical determinant for the attack of the triamine dimers by BSAO. Moreover, these data demonstrate that BSD and BNSD compounds are remarkably inert toward cell proliferation in the absence of oxidative deamination. Aminoguanidine was therefore included in all growth media involving polyamine transport antagonists in order to prevent cytotoxicity resulting from BSAO activity. In the presence of aminoguanidine, all BSD and BNSD derivatives were shown to be chemically stable for at least 6 days at 37° C. in cell-free, serum-containing growth media (data not shown).

BNSD-X Potentiates DFMO-Induced Cytostasis in Mammalian Cells

Figures 5D, 5E, 5F:
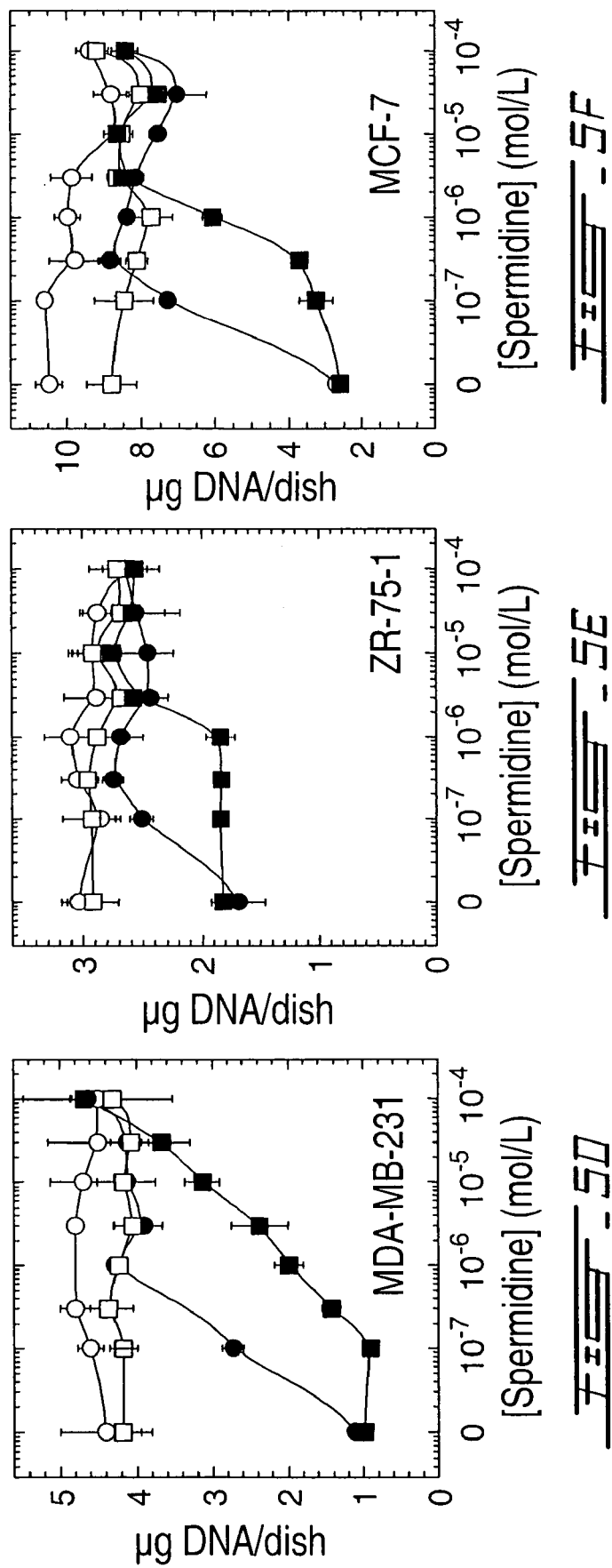
Figure 6A:
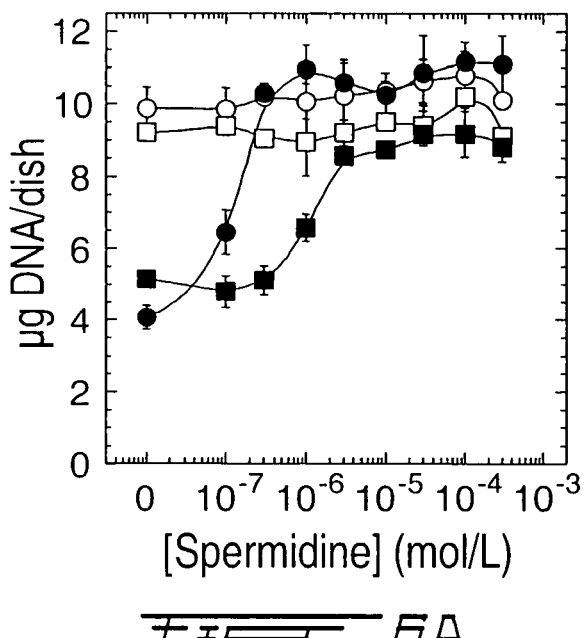
FIGS. 6A, 6B, 6C and 6D are graph showing that antagonism of DFMO-induced cytostasis by exogenous spermidine depends on the polyamine and linker structure of the compounds used in a method according to a preferred embodiment of the invention. In particular, T-47D cells were grown for 8-9 d with the indicated concentrations of spermidine in medium containing 1 mM aminoguanidine, in the presence of DFMO (●), transport inhibitor (□), DFMO plus transport inhibitor (■), or in the absence of either agent (○), and total DNA content per culture was then determined. Panels A, B, C, and D describe the effect of BNSD-X, BSD-X, BNSD-3 and BSD-3, respectively. Data are presented as the mean±SD for triplicate cultures from one out of at least two identical experiments.
Figure 6B:
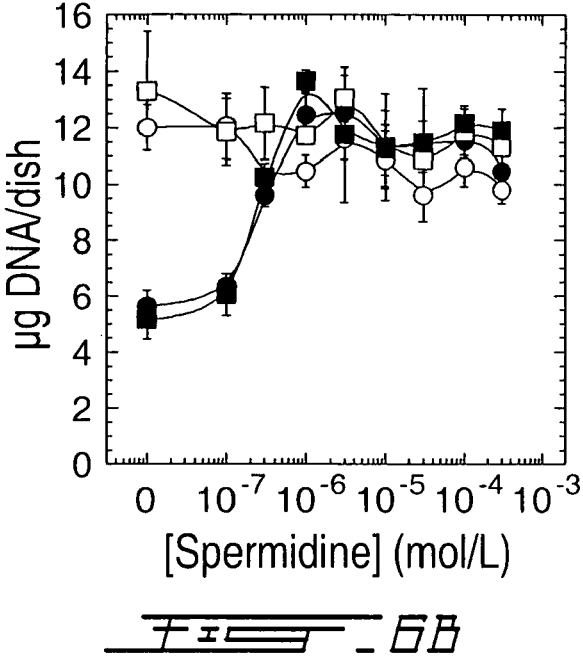

BNSD-X was singled out as one the most potent compounds among the novel spermidine and norspermidine dimers. A stringent assessment of the ability of a competitive polyamine transport antagonist to block polyamine uptake and accumulation is its capacity for preventing reversal of DFMO-induced cytostasis by exogenous polyamines during chronic incubation with cultured cells (U.S. Pat. No. 6,083, 496). Such a model mimics the counteracting effect of plasma polyamines on the in vivo efficacy of DFMO in the tumor microenvironment (Seiler et al. (1990) *Int. J. Biochem.* 22, 211-218); Persson et al. (1988) *Cancer Res.* 48, 4807-4811). We thus determined the relative ability of increasing concentrations of extracellular spermidine to reverse DFMO-induced inhibition of cell proliferation in the presence or absence of 50-100 µM BNSD-X in a variety of mammalian cell lines. As observed previously (U.S. Pat. No. 6,083,496), spermidine concentrations as low as 0.3-1 µM could completely counteract DFMO-induced cytostasis in most cell lines, i.e. at levels comparable to plasma concentrations found in human plasma (Ajani et al. (1989) *Cancer Res* 49, 5761-5). The concentration of BNSD-X used in each case had little or no effect on cell proliferation in cells treated with the inhibitor alone, except in L1210 mouse leukemia cells (FIG. 5C), and to a lesser degree, in MCF-7 human breast cancer cells (FIG. 5F). However, while DFMO decreased cell proliferation to various extents according to the cell type considered, BNSD-X increased by 10 to 100-fold the concentration of spermidine required to fully restore cell proliferation upon treatment with DFMO (FIGS. 5 and 6A). The combination of BNSD-X and DFMO inhibited cell proliferation to about the same extent as DFMO alone in the absence of exogenously added spermidine, except in CHO-K1 cells, where the dual treatment further depressed cell proliferation (FIG. 5A). It is noteworthy that increasing concentrations of exogenous spermidine did not prevent the inhibition of cell proliferation induced by BNSD-X observed in L1210 cells (FIG. 5C) or LAN-1 cells (data not shown), suggesting that the triamine dimer exerts its mild antiproliferative effect at a site that does not involve the polyamine transport system.

Figure 6C:
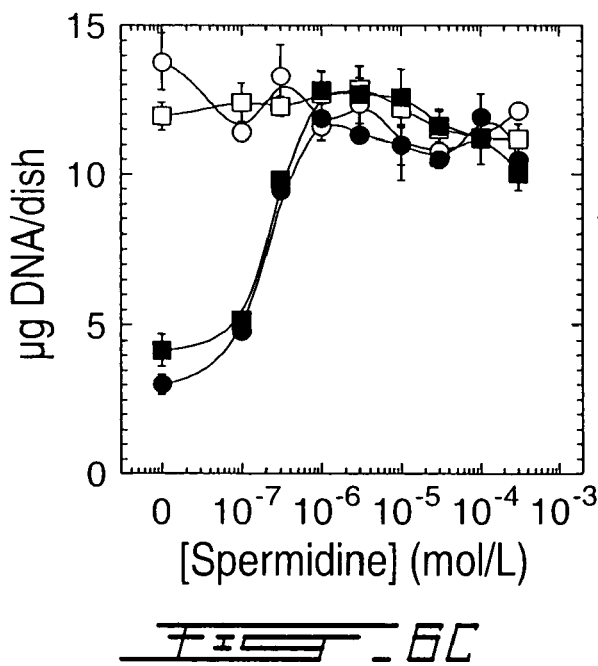
Figure 6D:
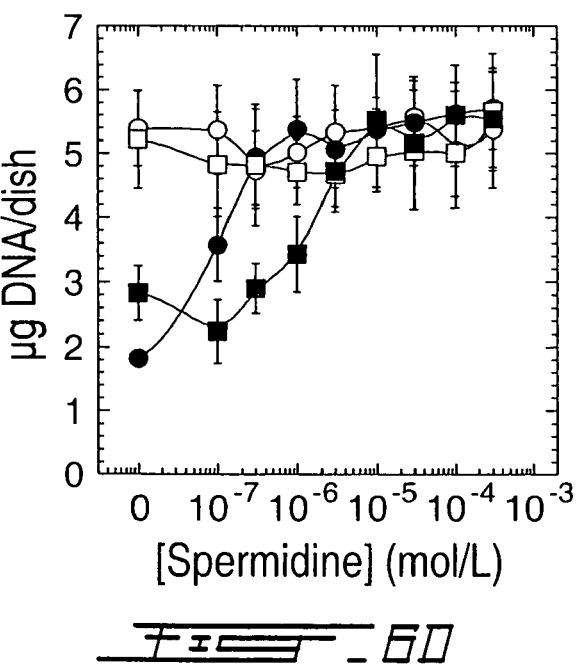

Other triamine dimers of the BSD or BNSD series should in principle exhibit the same potentiating effect as BNSD-X on DFMO-induced cytostasis in the presence of extracellular polyamines. Surprisingly, however, BSD-X, i.e. the spermidine-like homolog of BNSD-X, did not increase the range of spermidine concentrations able to reverse inhibition of cell proliferation by DFMO in T-47D cells (FIGS. 6A, B) in despite of a similar $K_i$ value against spermidine uptake activity (Table 1). Nevertheless, BSD-X activity against spermidine-mediated reversal of growth inhibition by DFMO was cell line-specific, since both BNSD-X and BSD-X afforded increased resistance to exogenous spermidine in DFMO-treated CHO-K1 cells (data not shown). On the other hand, BSD-3 significantly potentiated DFMO-induced cytostasis in T-47D (FIG. 6D) but not in CHO-K1 cells (data not shown)

incubated with extracellular spermidine, whereas the corresponding norspermidine derivative BNSD-3 which is about 5 times less potent than BSD-3 as a spermidine transport antagonist (Table 1), exhibited no activity in either cell line (FIG. 6C and results not shown). These data indicate that BSD and BNSD derivatives exhibit marked differences in their ability to potentiate DFMO action in the presence of extracellular spermidine, as a function of their relative potency as polyamine uptake inhibitors and of the cell type considered. Moreover, BNSD-X was the only compound among the BSD and BNSD derivatives to consistently protect against reversal of DFMO-mediated growth inhibition by exogenous spermidine.

Figures 7A, 7B, 7C:
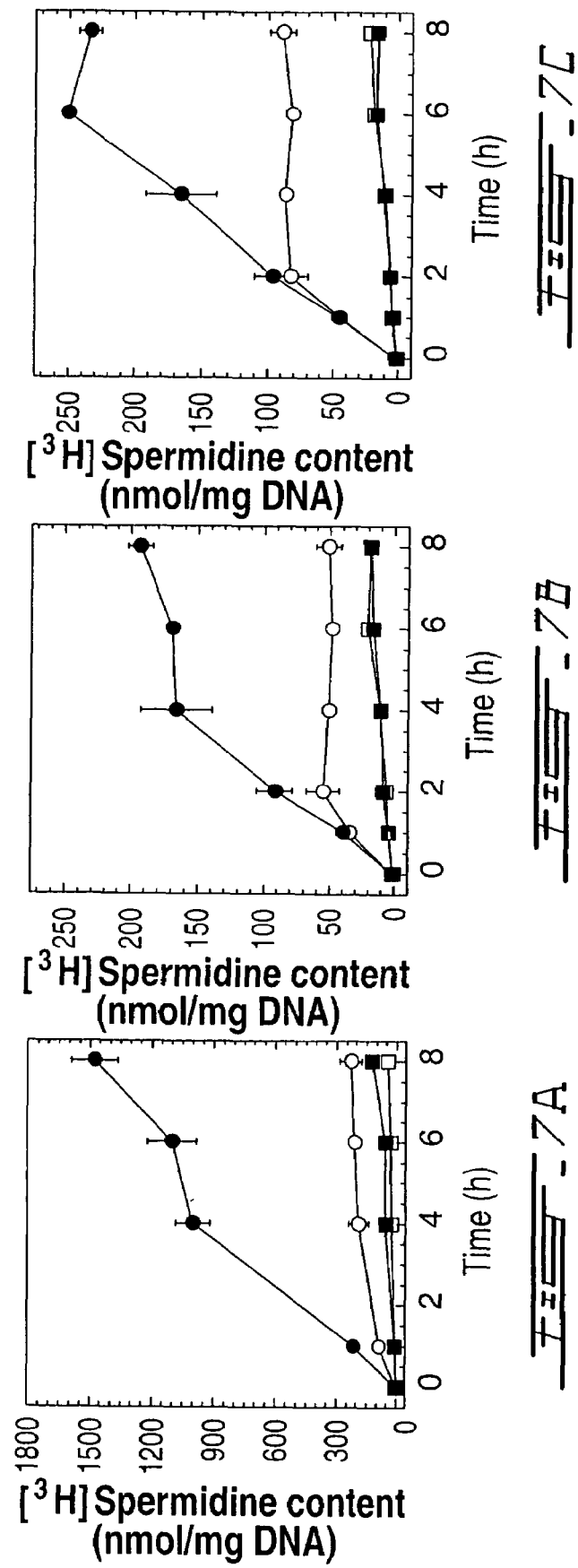
FIGS. 7A, 7B, and 7C are graph showing that a compound used in a method according to a preferred embodiment of the invention strongly inhibits accumulation of exogenous spermidine and its up-regulation by relief from feedback inhibition or by polyamine depletion. In particular, exponentially growing T-47D (A) or ZR-75-1 cells (B and C) were transferred to serum-free medium containing 5 μM [$^3$H]spermidine, and either 200 μM cycloheximide (CHX) (●), 100 μM BNSD-X (□), CHX plus BNSD-X (■), or vehicle only (○). Cells were incubated for the time intervals indicated prior to harvesting for detrmination of total intracellular radioactivity. ZR-75-1 cells were either pre-incubated for 48 h in the absence (panel B) or presence of 1 mM DFMO (panel C) prior to the experiment shown; DFMO was also included during the labeling period in the appropriate group. Data are presented as the mean±SD for triplicate cultures from one representative experiment.

The effect of BNSD-X on the time course of [$^3$H]spermidine accumulation was determined in ZR-75-1 and T-47D cells pre-incubated in the presence or absence of DFMO before addition of radioactive substrate and the transport inhibitor. Subgroups of cell cultures were also treated with cycloheximide in order to prevent the polyamine-dependent induction of ODC antizyme, which rapidly down-regulates polyamine transport activity through an unknown mechanism (Lessard et al. (1995) *J. Biol. Chem.* 270, 1685-1694; Coffino et al. (2001) *Nat Rev Mol Cell Biol.* 2:188-194). As expected, [$^3$H]spermidine accumulation reached a plateau after approximately 2 h in both ZR-75-1 (FIG. 7A) and T-47D control cells (FIG. 7B), but increased in an approximately linear fashion for the first 6-8 h in the presence of cycloheximide, consistent with relief from feedback repression of polyamine transport as a result of inhibition of antizyme synthesis. At a BNSD-X:spermidine ratio of 20:1, the triamine dimer decreased net [$^3$H]spermidine uptake in T-47D cells after 8 h by 92% and 80% in the presence or absence of cycloheximide, respectively (FIG. 7A), whereas it inhibited spermidine accumulation by 90 and 65%, respectively, under the same conditions in ZR-75-1 cells (FIG. 7B). DFMO-treated ZR-75-1 cells exhibited an increase in the initial velocity of [$^3$H]spermidine transport, in agreement with previous reports (Lessard et al. (1995) *J. Biol. Chem.* 270, 1685-1694; U.S. Pat. No. 6,083,496) and with the fact that polyamine depletion upregulates the activity of the mammalian transport system (Lessard et al. (1995) *J. Biol. Chem.* 270, 1685-1694; Seiler et al. (1990) *Int. J. Biochem.* 22, 211-218; Marton et al. (1995) *Ann. Rev. Pharmacol. Toxicol.* 35, 55-91). Nevertheless, BNSD-X inhibited net [$^3$H]spermidine uptake by the same extent in control and DFMO-treated ZR-75-1 cells, either in the presence or absence of cycloheximide (FIGS. 7B and C). Thus, BNSD-X substantially inhibits polyamine accumulation in mammalian cells, even upon prior depletion of the polyamine pool by DFMO treatment. However, a low, residual rate of spermidine influx subsists even in the presence of a 20-fold excess of BNSD-X, corresponding to 8-10% of the maximal rate of spermidine accumulation, and that might account for the fact that complete prevention of reversion of DFMO-induced cytostasis by spermidine was generally observed at a BNSD-X:spermidine ratio greater than 50:1 (cf. FIG. 5).

Mechanism of Potentiation of DFMO Action by BNSD-X

Figure 8B:
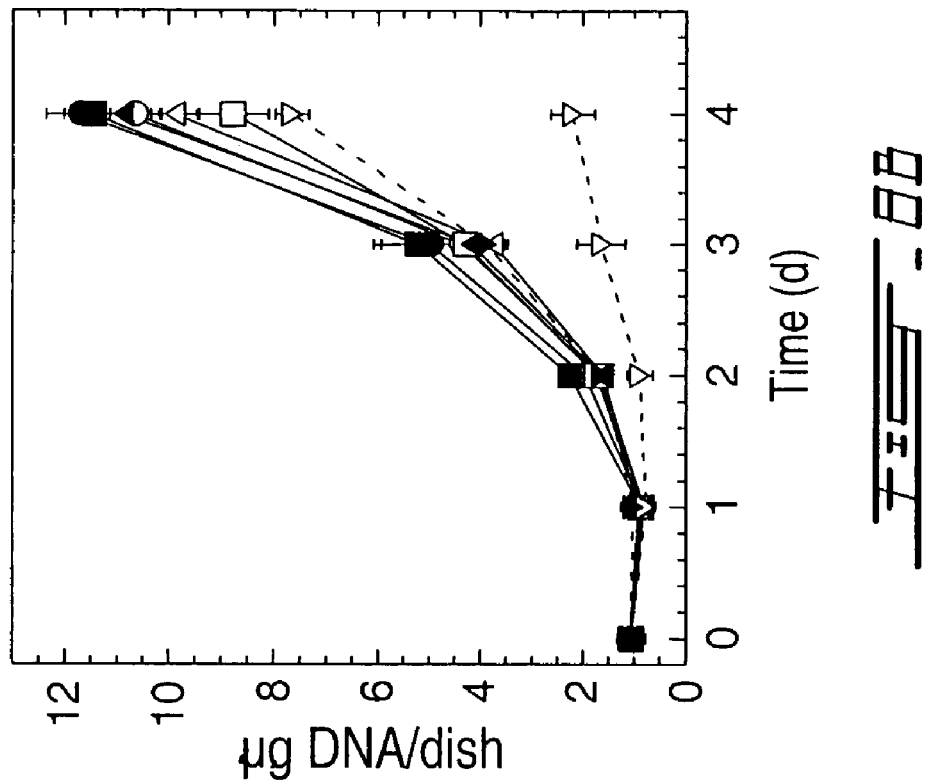
FIGS. 8A and 8B are graphs representing the time course of the effect of a compound used in a method according to a preferred embodiment of the invention on rescue of DFMO-induced cytostasis by exogenous spermidine. In particular, at time zero, T-47D (panel A) or CHO-K1 (panel B) were seeded at $1\times10^4$ or $5\times10^3$ cells/well, respectively, in medium containing 1 mM aminoguanidine, plus either 0.3 μM spermidine (Spd, ●), 2 mM DFMO (□), Spd+DFMO (■), 50 μM (A) or 100 μM (B) BNSD-X (Δ), BNSD-X+Spd (▲), BNSD-X+DFMO (◇), BNSD-X+Spd+DFMO (▼), or vehicle only (○). At the indicated time, total DNA content/well was determined. Data are presented as the mean±SD for triplicate cultures from one representative experiment.
Figure 8A:
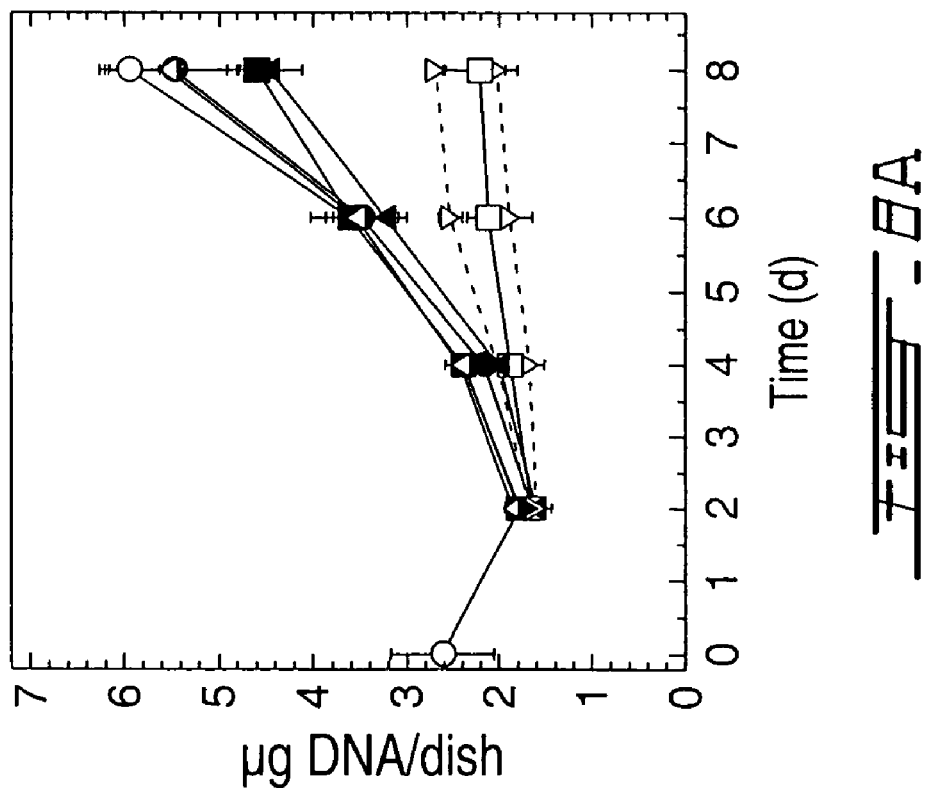

The above data indicate that BNSD-X and similar derivatives did not further enhance cytostasis induced by DFMO in the absence of exogenous polyamines in most cell lines examined, but merely increased the spermidine concentration required for reversal of DFMO-induced growth inhibition. This effect would be expected if the triamine dimers merely behave as pure competitive inhibitors of polyamine uptake. The latter hypothesis is in agreement with the time course of BNSD-X action on cell proliferation observed in T-47D cells (FIG. 8A). Thus, whereas the addition of 0.3 μM spermidine immediately prevented cytostasis induced by DFMO in these cells, supplementation with a 167-fold excess of BNSD-X counteracted normalization of cell proliferation by exogenous spermidine but did not markedly increase the extent of growth inhibition observed with DFMO alone (FIG. 8A), even at suboptimal concentrations of DFMO (data not shown). In contrast, in addition to blocking the reversal of DFMO-induced cytostasis by spermidine in CHO-K1 cells, BNSD-X strongly potentiated the antiproliferative effect of DFMO in the nominal absence of exogenous polyamines in a synergistic fashion (FIG. 8B). The latter data suggest that BNSD-X might not only act as a competitive inhibitor of polyamine uptake, but might also amplify polyamine depletion induced by DFMO, at least in some cell types.

Figure 9B:
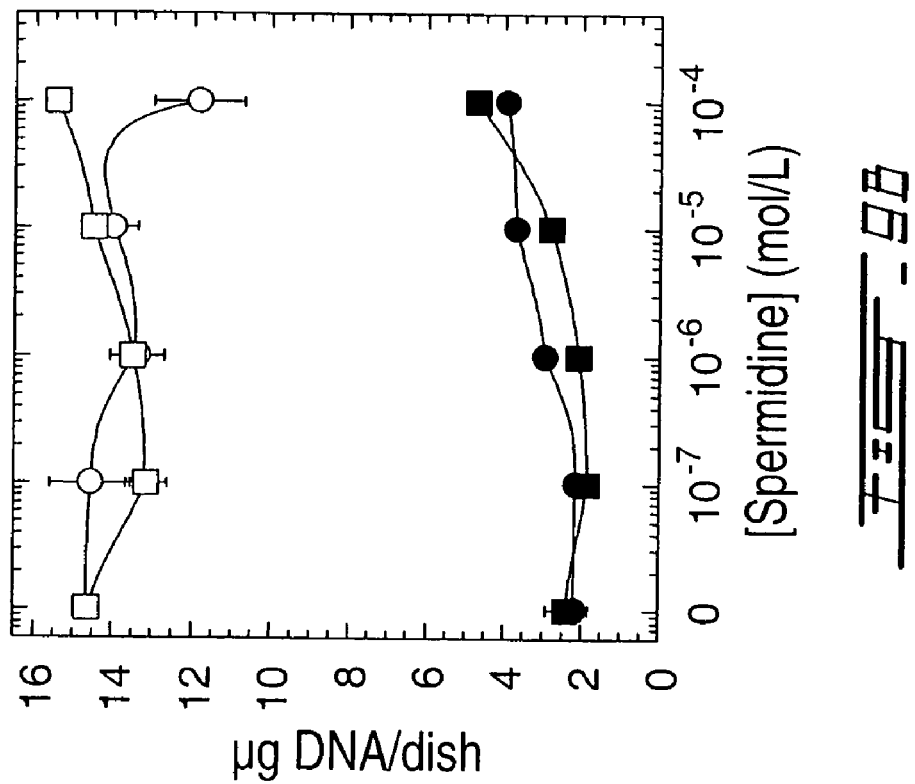
FIGS. 9A and 9B are graphs showing that potentiation of DFMO-induced cytostasis by a compound used in a method according to a preferred embodiment of the invention requires a functional polyamine transport system. In particular, CHO-TOR cells (A) and their polyamine transport-deficient mutant subline CHO-MG (B) were grown in medium containing 1 mM aminoguanidine and the indicated concentration of spermidine, in the presence of 2 mM DFMO (●), BNSD-X (□), DFMO+BNSD-X (■), or vehicle only (○). Cells were harvested after 4 d for determination of total DNA/well. Data are presented as the mean±SD for triplicate cultures from one representative experiment.
Figure 9A:
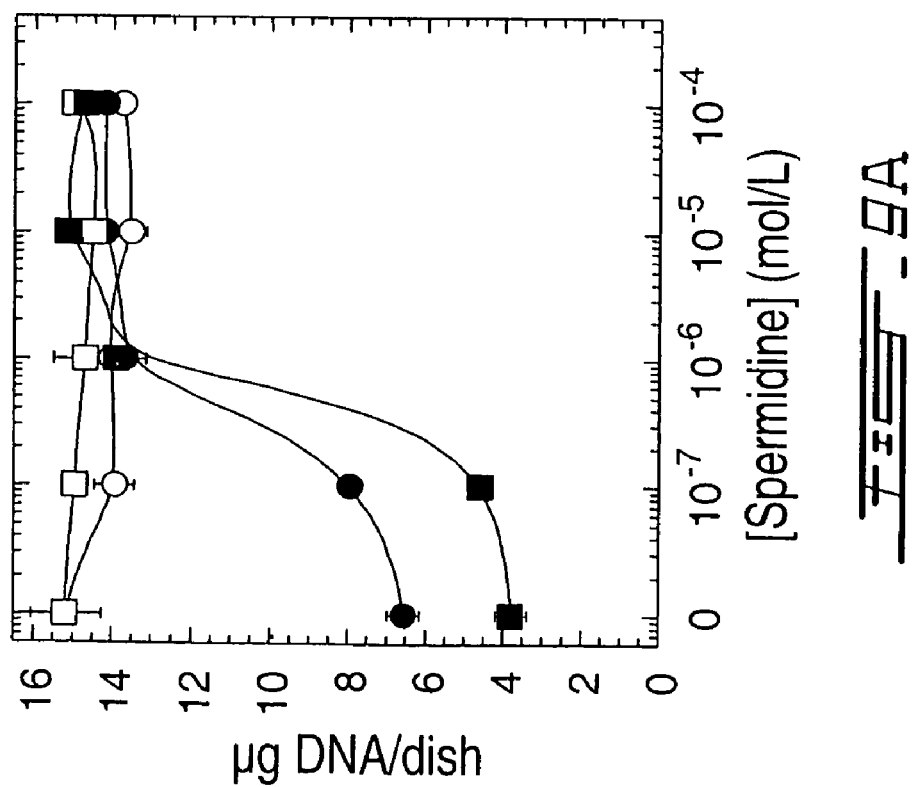

To further characterize the mechanism of action of BNSD-X in CHO cells, we compared the effect of BNSD-X on cell proliferation in CHO-MG cells, which are genetically deficient in polyamine transport activity (Heaton et al. (1988) *J. Cell. Physiol.* 136, 133-139), and their parental strain (CHO-TOR). As shown in FIG. 9, potentiation of DFMO-induced cytostasis by BNSD-X in the absence of exogenous spermidine was observed in the parental cell line, but not in the polyamine transport mutant. In CHO-MG cells, high concentrations of spermidine induced a very limited reversal of growth inhibition by DFMO which was antagonized by BNSD-X (FIG. 9B), in agreement with the strong polyamine transport defect present in these mutants. The latter results clearly indicate that a functional polyamine carrier is required for the synergistic effect of BNSD-X on the antiproliferative action of DFMO in CHO cells.

Figures 10A, 10B, 10C:
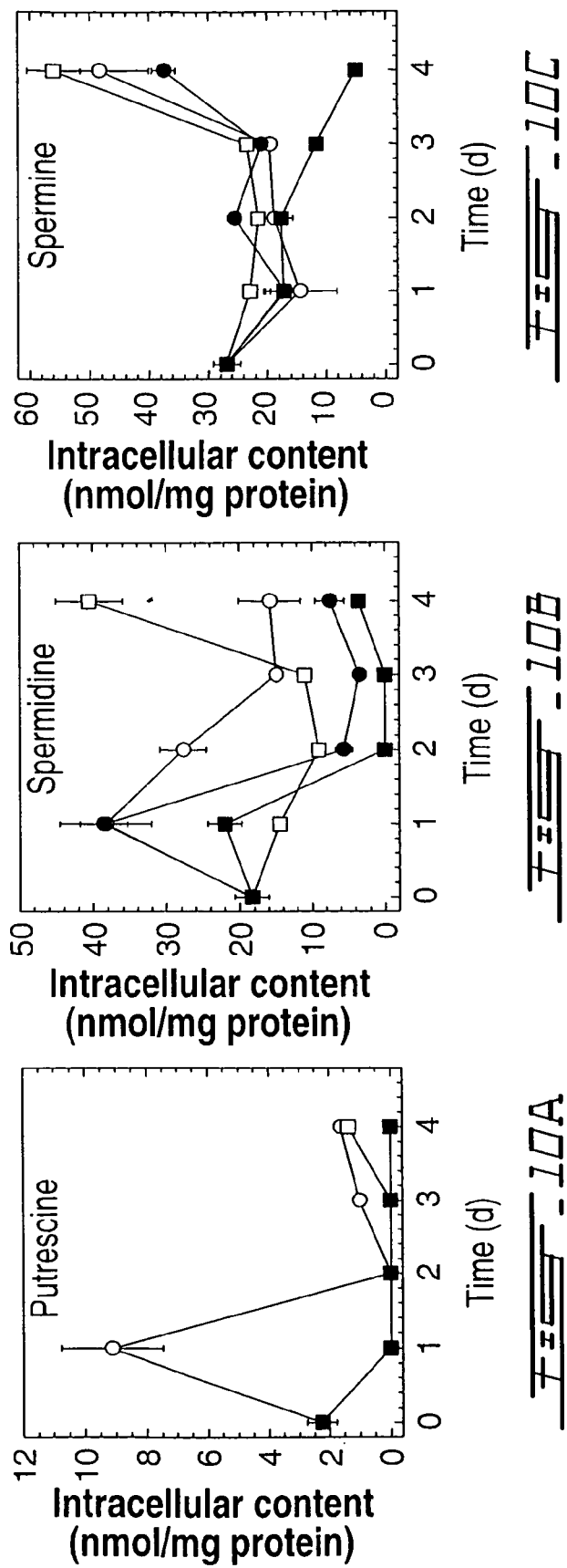
FIGS. 10A, 10B and 10C are graphs showing that a compound used in a method according to a preferred embodiment of the invention potentiates DFMO-induced cytostasis by promoting spermidine and spermine depletion. In particular, at time zero, CHO-K1 cells (1.5×10⁵ cells) were seeded in 100-mm dishes in medium containing 1 mM aminoguanidine, in the presence of either 2 mM DFMO (●), 100 μM BNSD-X (□), DFMO+BNSD-X (■), or vehicle only (○). At the indicated time, cells were harvested for the determination of putrescine (A), spermidine (B) and spermine contents (C). Data are presented as the mean±SD for triplicate cultures from one representative experiment.

The effect of BNSD-X on the intracellular putrescine and polyamine contents was next determined in CHO-K1 cells incubated for 4 days in the presence of DFMO and/or transport antagonist (FIG. 10) in order to assess possible effects of the drug on polyamine homeostasis. The sole addition of DFMO rapidly led to putrescine depletion (FIG. 10A), and after a 24-h lag period, decreased the spermidine pool by 80% (FIG. 10B), but had little effect on spermine content (FIG. 10C), as expected (Marton et al. (1995) *Ann. Rev. Pharmacol. Toxicol.* 35, 55-91). Surprisingly, BNSD-X alone also quickly led to putrescine depletion and reduced spermidine content by about 50% over the first 2 days of incubation, followed by a massive increase in the size of the spermidine pool between 3 and 4 days, while preventing the initial increase in spermidine content observed at the onset of exponential growth. BNSD-X had no significant effect on spermine content. On the other hand, coincubation with BNSD-X and DFMO increased both the rate and extent of spermidine depletion, while causing a dramatic decrease in intracellular spermine concentration.

These results suggest that BNSD-X potently amplifies the antiproliferative action of DFMO in CHO cells by inducing spermine depletion and by increasing the rate of reduction of spermidine content resulting from the inhibition of putrescine biosynthesis by the ODC inhibitor.

Synthesis of Spermine Dimers

As shown in FIG. 11, synthesis of these spermine dimers was carried out as previously defined concerning the spermidine and norspermidine derivatives. As example, for compound of formula 32e wherein the R group is xylene, the compound was prepared as follows: primary groups of the tetraamines 29 were regioselectively protected with trityl chloride in the presence of diethylamine. The spermine 30 was protected using 3 equiv of trityl chloride, thus leaving two free secondary amino group. The following steps of the synthesis (steps (b) and (c)), including coupling with α,α'-dibromo-p-xylene, and acidic hydrolysis of the trityl groups were carried out as previously described. Final purification of the products was carried out by cation exchange chromatography using Dowex 50X8-100, thus yielding compound 32e (BSM-X) as the hydrochloride salts. The compound 32e was caracterized as follows: $^1$H-NMR (D$_2$O): 7.61 (s, 4H, aromatic-H), 4.45 (s, 4H, 2×CH$_2$Ph), 3.25 (m, 8H, 4×CH$_2$N$^{III}$), 2.95-3.15 (m, 16H, 4×CH$_2$N$^{II}$, 4×CH$_2$N$^{I}$), 2.00-2.15 (m, 8H, 4×CH$_2$), 1.85 (m, 4H, 2×CH$_2$), 1.73 (m, 4H, 2×CH$_2$).

The potency of the polyamines and their xylylated dimers as competitive inhibitors of spermidine transport was evaluated in the T-47D human breast cancer cell line (Table 2).

TABLE 2

$K_i$ values for the inhibition of spermidine transport by a spermine dimer (32e) linked through a xylyl group in T-47D human breast cancer cells.

| Compounds | Substrates Or Inhibitors | $K_m$ or $K_i^a$, μM |
|---|---|---|
| | Putrescine (1,4-diaminobutane) | >500 |
| | Spermidine (3-4-TA) | 4.4 ± 0.9$^c$ |
| 29 | Spermine | 2.1 ± 0.2 |
| 32$^e$ | BSM-X | 1.1 ± 0.1 |

$^a$K$_i$ values were calculated from the half-maximal inhibitory concentration (IC$_{50}$) estimated by iterative curve fitting for sigmoidal equations describing spermidine uptake velocity in the presence of growing concentrations of antagonist.
$^b$Data are presented as the mean ± SD of two independent determinations of IC$_{50}$ values, each based on triplicate determinations of uptake velocity at increasing inhibitor concentrations.
$^c$The K$_m$ for spermidine uptake was independently determined by Lineweaver-Burke analysis of transport velocity data at increasing substrate concentrations (0.01-300 μM).

Likewise, the spermine dimer BSM-X (32e) had a 2-fold lower apparent K$_i$ for spermidine uptake inhibition relative to the spermine monomer. Thus, the increase in the number of cationic centers generated by dimerizing two diamines dramatically improves the ability of the resulting conjugate to interact with the polyamine carrier.

In Vivo Evaluation of the Pharmacological Efficacy of BNSD-X

Figure 12:
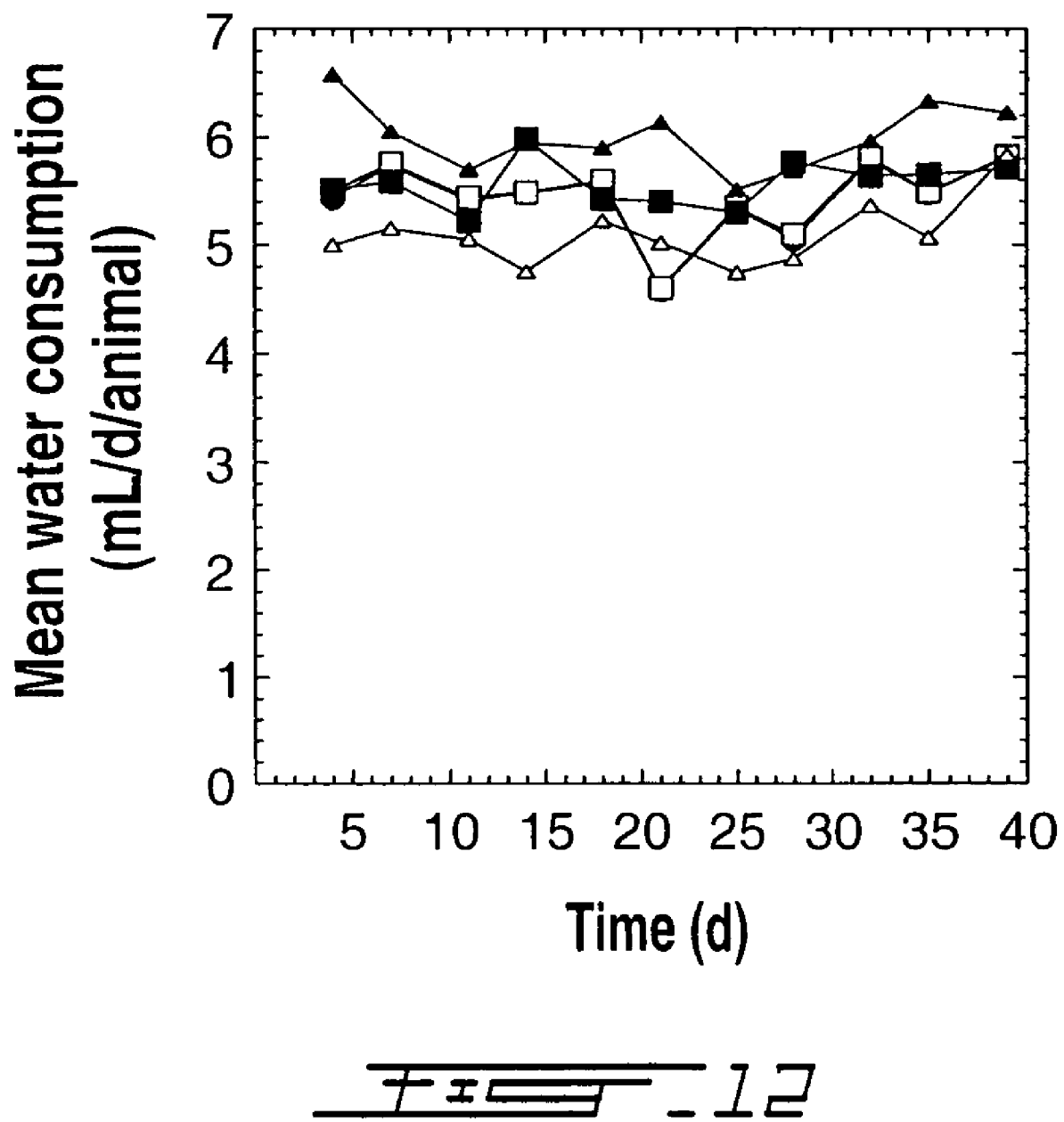
FIG. 12 shows the time course of H$_2$O consumption in immunodeficient CD-1 mice xenografted with MDA-MB-231 human breast cancer cells in the mammary fat pads and treated with compounds used in a method according to a preferred embodiment of the invention. In particular, the mice have been treated with the following compounds: BNSD-X (1% w/v) (●), 0.3 (w/v) DFMO (□), 0.3% DFMO+BNSD-X (■), 1% (w/v) DFMO (Δ), or 1% DFMO+BNSD-X (▲). Drugs were dissolved in drinking water which was given ad libitum to the animals. Control mice (○) received distilled water only.

The suitability of BNSD-X as an in vivo inhibitor of polyamine transport was next assessed in the mouse. We first determined the bioavailability of the compound by adding escalating doses of BNSD-X (0, 0.25, 0.5, 1.0, 2.0 and 4.0% (w/v)) in the drinking water of CD-1 mice. Mice were sacrificed after 4 d and the concentration of BNSD-X and polyamines was determined in plasma and erythrocytes (Tables 3 and 4). The two highest BNSD-X concentrations (2.0 and 4.0%) could not be used since water consumption decreased drastically at concentrations higher than 1.0% (FIG. 12). BNSD-X was readily absorbed orally and plasma levels of the drug reached a concentration of 129±33 nM, i.e. a value close to that of the main plasma polyamine, namely spermidine (Table 0.3). When solid BNSD-X was administered by gavage (1 g/kg body weight), BNSD-X could be detected in the plasma after 1 h, reaching a concentration of 450±71 nM (n=5), with a half-life >6 h. The plasma concentration reached by the chronic drinking of a 1% (w/v) solution of BNSD-X is thus approximately equal to the Ki value of the drug as an inhibitor of spermidine uptake in breast cancer cells (see Table 1). The drug had no effect on the plasma concentration of either putrescine, spermidine or spermine. Furthermore, BNSD-X (up to 1.0%) did not accumulate into erythrocytes nor significantly affect spermidine or spermine contents in red blood cells (Table 4). These results demonstrate that BNSD-X is an orally available drug that is readily absorbed by the gastrointestinal tract as an aqueous solution, and that reaches plasma concentrations close to that of the main plasma polyamine, i.e. spermidine. These pharmacokinetic properties indicate that BNSD-X can be administered by a very convenient route to animals up to a dose sufficient in principle to inhibit the major fraction of the uptake of spermidine from the plasma.

TABLE 3

Plasma concentrations of polyamines and BNSD-X after 96 h of ad libitum oral delivery of BNSD-X in drinking water in CD-1 mice.

| [BNSD-X] | Plasma concentration (nM)$^1$ | | | |
|---|---|---|---|---|
| (%, w/v) | Putrescine | Spermidine | Spermine | BNSD-X |
| 0 | 107 ± 3 | 136 ± 20 | 21 ± 2 | — |
| 0.25 | 108 ± 11 | 147 ± 6 | 24 ± 1 | 6 ± 3 |
| 0.50 | 106 ± 10 | 137 ± 18 | 31 ± 6 | 32 ± 6 |
| 1.0 | 117 ± 19 | 168 ± 15 | 38 ± 3 | 129 ± 33 |

$^1$Data are expressed as the mean ± S.E. for 6 animals/group.

TABLE 4

Erythrocyte concentrations of polyamines after 96 h of ad libitum oral delivery of BNSD-X in drinking water in CD-1 mice.

| | Erythrocyte concentration (nmol/L packed erythrocytes)$^1$ | |
|---|---|---|
| [BNSD-X] (%, w/v) | Spermidine | Spermine |
| 0 | 2713 ± 474 | 134 ± 50 |
| 0.25 | 1975 ± 236 | 60 ± 14 |
| 0.50 | 2762 ± 560 | 95 ± 12 |
| 1.0 | 2079 ± 291 | 83 ± 23 |

$^1$Putrescine and BNSD-X were undetectable (<50 and 25 nmol/L of packed erythrocytes).
$^2$Data are expressed as the mean ± S.E. for 6 animals (except for the 0.25% BNSD-X group for which 5 animals were used).

Orally administered polyamines (at ≧0.6 g/kg/day) can have deleterious neurological effects and induce lesions on internal organs (Til et al. (1997) Food Chem Toxicol. 35:337-348.). In order to assess the acute and subacute toxicity of BNSD-X as an orally delivered hexaamine, the effects of gavage with solid BNSD-X pellets was first examined in mice. No external sign of sign of adverse effect on animal behavior, body weight, body features and the gross anatomy of kidneys, liver or spleen could be observed up to 5.0 g/kg body weight, which indicates (LD$_{50}$>5 g/body weight) that BNSD-X is practically non-toxic or relatively harmless, according to accepted criteria for animal toxicity studies (Li et al. (2004) Chem Biol Interact. 150:27-33).

The chronic toxicity of BNSD-X was next evaluated by allowing CD-1 mice to drink a 1% (w/v) solution of the drug for 14 d, and then sacrificing animals for the histological examination of the liver, kidneys and spleen. The chronic administration of BNSD-X had no incidence on the behavior nor general body appearance of the animals. The chronic administration of BNSD-X had no incidence on the behavior nor general body appearance of the animals. There was no observable differences in the histological morphology of the liver, kidney and spleen as observed by light microscopy (not shown).

Figure 14:
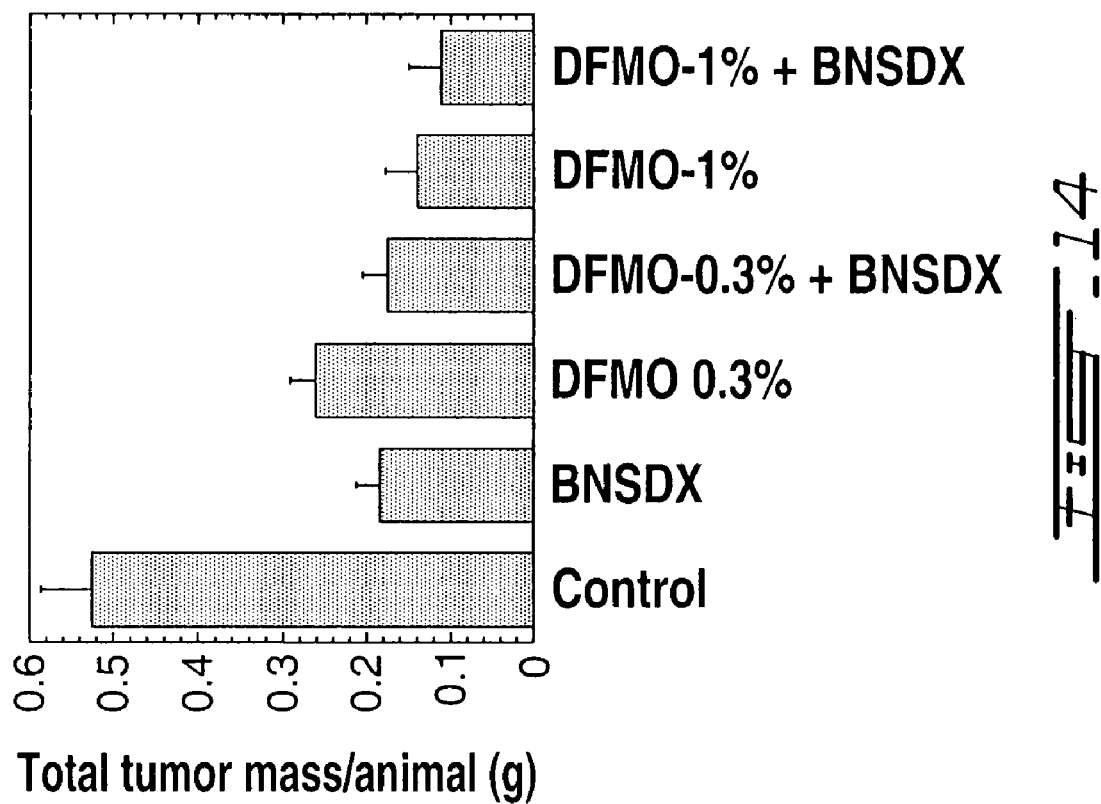
FIG. 14 shows the effect of a 39-d treatment with compounds used in a method according to a preferred embodiment of the invention on the total mass of MDA-MB-231 human breast tumors growing as xenografts in immunodeficient CD-1 mice. In particular, these compounds are BNSD-X (1% w/v), 0.3 (w/v) DFMO, 0.3% DFMO+BNSD-X, 1% (w/v) DFMO, or 1% DFMO+BNSD-X Drugs were dissolved in drinking water which was given ad libitum to the animals. Control mice received distilled water only.
Figure 13:
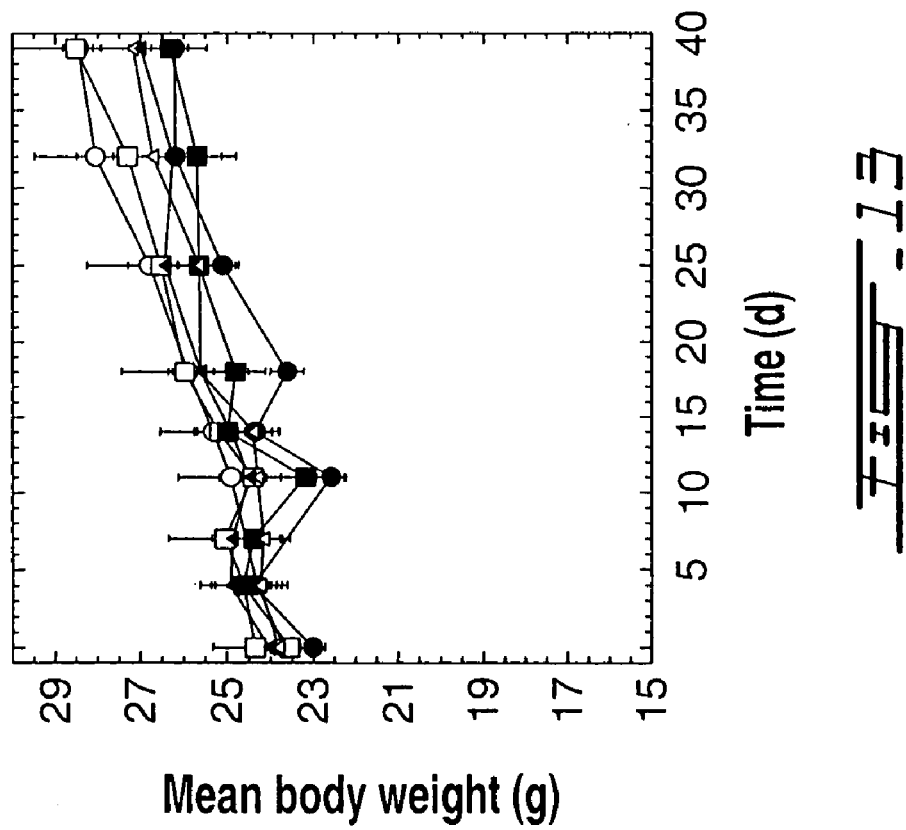
FIG. 13 shows the time course of body mass in immunodeficient CD-1 mice xenografted with MDA-MB-231 human breast cancer cells in the mammary fat pads and treated with compounds used in a method according to a preferred embodiment of the invention. In particular, the mice have been treated with the following compounds: BNSD-X (1% w/v) (●), 0.3 (w/v) DFMO (□), 0.3% DFMO+BNSD-X (■), 1% (w/v) DFMO (Δ), or 1% DFMO+BNSD-X (▲). Drugs were dissolved in drinking water which was given ad libitum to the animals. Control mice (○) received distilled water only.

The efficacy of BNSD-X as a chemotherapeutic agent was assessed in the MDA-MB-231 model of human breast cancer xenograft in the nude mouse, a model which is known to be sensitive to polyamine depletion by DFMO (Weeks et al., (2000) *Exp Cell Res.* 261:293-302). For that purpose, MDA-MB-231 cells were injected in the left and right mammary fat pads of immunodeficient CD-1 mice. Mice were then allowed to drink either BNSD-X at the optimal concentration (1%, w/v), as well as DFMO at either 0.3% or 1% (w/v) plus or minus 1% BNSD-X for 39 days before sacrificing the animals and measuring total final tumor mass (FIG. 12-14). The BNSD-X solution alone or with 0.3% DFMO led to a slight (~7%) reduction of body weight, which was attenuated by the addition of 1% DFMO (FIG. 13) However, this effect of body weight could largely be accounted on the decreased tumor burden in the BNSD-X treated animals (FIG. 14). Water consumption was not adversely affected by any treatment except the 1% DFMO solution, an effect which was reversed by the simultaneous addition of 1% BNSD-X (FIG. 12). In marked contrast with its lack of antiproliferative activity in cultured cancer cells in vitro, BNSD-X as a single agent decreased total tumor mass in xenografted CD-1 mice by 65±10% after a 39-d treatment (FIG. 14). Moreover, BNSD-X potentiated the action of DFMO at the 0.3% concentration, the combination reducing the tumor burden by 67±6% vs. 50±6% with DFMO alone (0.3%). Furthermore, BNSD-X amplified the anti-tumor effect of the higher concentration of DFMO (1%) from 73±7 to 79±7% growth inhibition (FIG. 14).

These data clearly demonstrate that BNSD-X can be administered per os together with DFMO in a convenient pharmacological route and dosage form that has little, if any adverse effect at a dose which achieves steady-sate plasma concentrations of the drug which are sufficient to inhibit most of spermidine transport as based on determinations of the kinetic parameters of transport inhibition by the compound. Moreover, BNSD-X exhibits intrinsic antitumor activity in the MDA-MB-231 human xenograft model in nude mice, a property that was not observed in cultured mammalian cell models. The unexpected antitumor effect of BNSD-X per se may be interpreted as the result of blocking a significant influx of circulating plasma polyamines in the tumor environment (Duranton et al., (1997) *Cancer Res.* 57:573-575). Finally, the examples provided show that the combination of DFMO and BNSD-X might be advantageous from the potentiation of the therapeutic effect of DFMO by the transport inhibitor, as seen from the in vivo studies provided as examples.

The utility of the present invention is by no means restricted to blocking the cancer types for which the effectiveness of the invention has been demonstrated in the above examples. Since the present invention relies on preventing the internalization of polyamines, the treatment of any disorder for which evidence exists that polyamine depletion could contribute to its prevention and/or therapy thus falls within the scope of the present invention.

The present invention can be reasonably expected to be useful the treatment of virtually all types of cancerous diseases, as supported by the extensive literature on the experimental treatment of cancer (Gerner et al. (2004) *Nat Rev Cancer.* 4:781-792). Virtually every type of neoplastic diseases has been shown to be antagonized by polyamine depletion induced by agents such as DFMO. Therefore, the ability of the present invention to potentiate the effect of DFMO predicts that the invention can be useful for the treatment of most, if not all types of cancers (Gerner et al. (2004) *Nat Rev Cancer.* 4:781-792; Seiler, N. (2003) *Curr Drug Targets.* 4:537-564; Seiler, N. (2003) *Curr Drug Targets.* 4:565-585). Following similar lines of reasoning, knowledge of the art predicts that the present invention will be useful for enhancing the ability of DFMO to prevent many types of cancer in patients at risk, i.e. the use of the method for the chemoprevention of cancer. The demonstrated, albeit partial effectiveness of DFMO as a chemopreventive agent is very likely to be substantially increased by preventing the reversal of its action with a polyamine transport inhibitor. (Gerner et al. (2004) *Nat Rev Cancer.* 4:781-792; Meyskens et al. (1999) *Clin Cancer Res.* 5:945-951; Seiler, N. (2003) *Curr Drug Targets.* 4:537-564; Seiler, N. (2003) *Curr Drug Targets.* 4:565-585).

Intracellular polyamines control the gating of several ion channel types, especially potassium channels, and modulate the conductance of glutamate receptor-regulated channels of the N-methyl-D-aspartate and α-amino-3-hydroxyl-5-methyl-4-isoxazole-propionate (AMPA)/kainate types (Lu, Z. (2004) *Annu Rev Physiol.* 66:103-129; Johnson, T. D (1996) *Trends Pharmacol. Sci.* 17:22-27; Williams, K. (1997) *Biochem. J.* 325:289-297). Furthermore, polyamines are known to promote and accelerate the formation of Lewy bodies, an important feature responsible for neurodegenerative complications of Parkinson's disease (Antony et al. (2003) *J Biol Chem.* 278:3235-3240). Taken together, these effects predicted that polyamine depletion by agents such as DFMO might have a beneficial in the therapy and management of various neurological disorders, and experimental evidence strongly supports these premises (Bianchi et al. (1996) *J. Biol. Chem.* 271:6114-6121; Li et al. (2004) *Brain Res.* 1029: 84-92; Soulet et al. (2003) *J. Cell Biol.* 162:257-268; Taglialatela et al. (1995) *Pharmacol Res.* 32:335-344.). Therefore, a usefulness of the present invention can be reasonably predicted for the treatment and management of neurodegenerative disorders or complications such as Alzheimer's disease (Yatin et al. (2001) *J Neurosci Res.* 63:395-401), amyotrophic lateral sclerosis, (Gomes-Trolin et al. (2002) *Exp Neurol.* 177:515-520). Parkinson's disease, (Antony et al. (2003) *J Biol Chem.* 278:3235-3240; Gomes-Trolin et al. (2002) *Exp Neurol.* 177:515-520) and cerebral ischemia (Li et al. (2004) *Brain Res.* 1029:84-92). Likewise, neurological disorders resulting from abnormal cellular excitability due to aberrant potassium channel rectification, such as epilepsy, are likely candidates for the beneficial effects of the potentiation of polyamine depletion by the present invention (Bianchi et al. (1996) *J. Biol. Chem.* 271:6114-6121; Li et al. (2004) *Brain Res.* 1029:84-92).

Polyamine depletion induced by DFMO has been shown to have beneficial effects in the treatment of autoimmune disorders such as psoriasis (McCullough et al. (1985) *J Invest Dermatol.* 85:518-521; Wallace et al. (2004) *Amino Acids.* 26:353-365.) and systemic lupus erythematosus (Gunnia et al. (1991) *Kidney Int.* 39:882-890). Therefore, the principle underlying the mechanism of action of our present invention reasonably anticipates its usefulness in the treatment of psoriasis and systemic lupus erythematosus.

The therapeutic efficacy of DFMO in the treatment and cure of sleeping sickness (African trypanosomiasis) has been clinically documented extensively. Moreover, there is ample support that polyamine depletion might be similarly useful in the treatment of other parasite-induced diseases, including other trypanosomiases (Yarlett, N. (1988) *Trichomonas vaginalis. Parasitol Today.* 4:357-360; Bacchi et al. (2002) *Mini Rev Med. Chem.* 2:553-563; Carrillo et al. (2000) *Biochem Biophys Res Commun.* 279:663-668), leishmaniases (Carrillo et al. (2000) *Biochem Biophys Res Commun.* 279:663-668), malaria (caused by *Plasmodium falciparum*) (Das et al. (1995) *Plasmodium falciparum. Pharmacol Res.* 31:189-193), vaginal trichomoniasis caused by *Trichomonas vaginalis* (Yarlett, N. (1988). *Parasitol Today.* 4:357-360) and *Pneumocystis carinii* pneumonia, a frequent complication of AIDS (Merali, S. (1999) *J. Biol. Chem.* 274:21017-21022). Thus, the need for improving the efficacy of DFMO-induced polyamine depletion clearly suggests the usefulness of the present invention in the treatment of infection by parasites such as *Trypanosoma* spp., *Leishmania* spp., *Plasmodium* spp., *Trichomonas* spp. and *Pneumocystis carinii*.

DFMO is currently marketed as a therapeutic agent against female hirsutism, especially in after menopause (Balfour et al. (2001) *Am J Clin Dermatol.* 2:197-201) (U.S. Pat. No. 4,720,489; U.S. Pat. No. 5,648,394)). However, the limited efficacy of this agent might benefit from the more thorough polyamine depletion favored by the present invention, and thus constitutes a further example of the usefulness of the present invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for inhibiting the activity of a natural polyamine transporter comprising the step of contacting said transporter with an inhibitorily effective amount of a compound of formula (I) or (II):

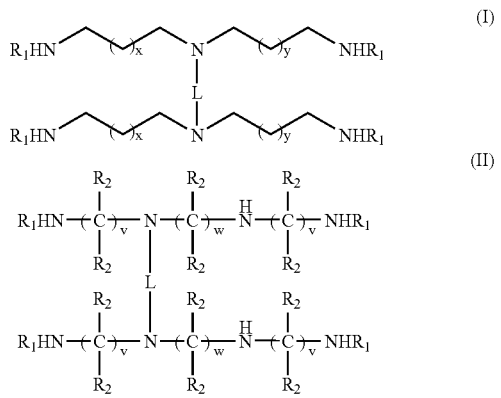

wherein
L is:

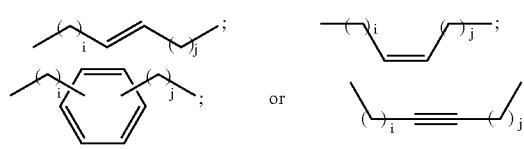

$R_1$=H, methyl, ethyl or propyl;
$R_2$=H or methyl;
$0<x<3$;
$0<y<3$;
$0<i<6$;
$0<j<6$;
$1 \leq i+j \leq 7$;
$2<v<5$; and
$2<w<8$.

2. The method of claim 1, wherein L is

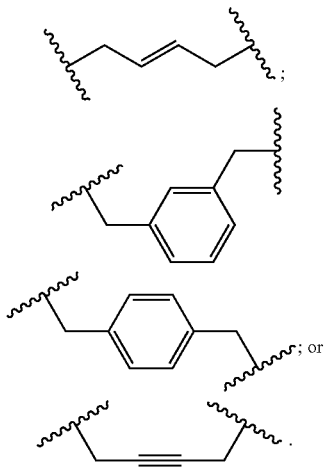

3. The method of claim 1, wherein L is

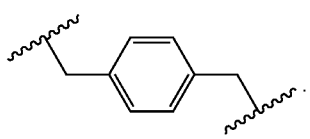

4. The method of claim 1, wherein said compound is administered per os to a patient.

5. The method of claim 1, wherein said compound is a compound of formula:

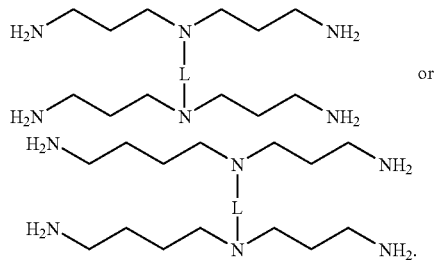

6. The method of claim 5, wherein L is

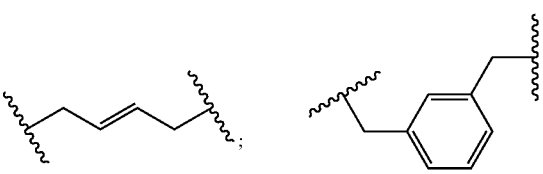

-continued

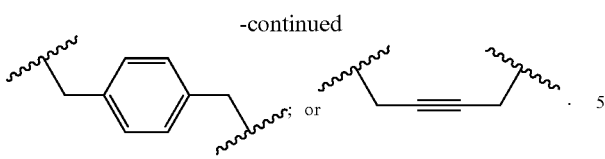

7. The method of claim 6, wherein L is

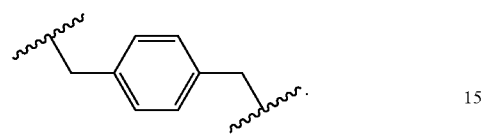

8. The method of claim 1, wherein the compound is administered in combination with an inhibitor of polyamine synthesis.

9. The method of claim 8, wherein the inhibitor of polyamine synthesis is α-difluoromethylornithine (DFMO).

10. A method for treating a disorder selected from leukemia and carcinoma of the breast, said method comprising the step of administering to a patient a therapeutically effective amount of a compound of formula (I) or (II):

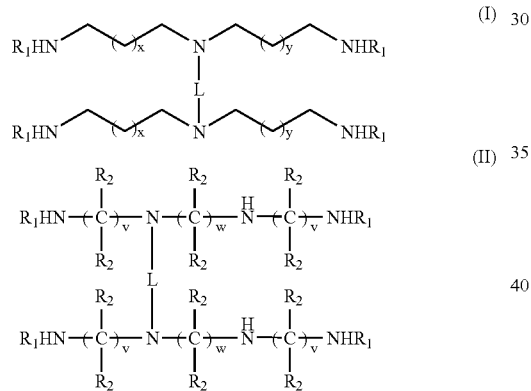

wherein
L is:

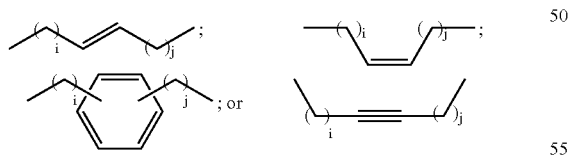

$R_1$=H, methyl, ethyl or propyl;
$R_2$=H or methyl;
$0<x<3$;
$0<y<3$;
$0<i<6$;
$0<j<6$;
$1 \leq i+j \leq 7$;
$2<v<5$; and
$2<w<8$.

11. The method of claim 10, wherein L is

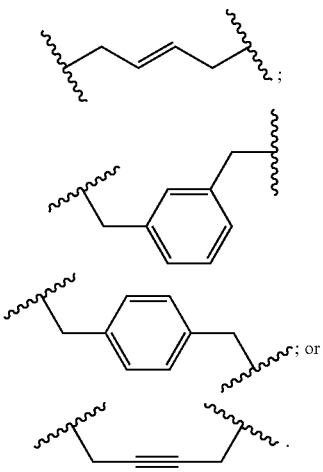

12. The method of claim 10, wherein L is

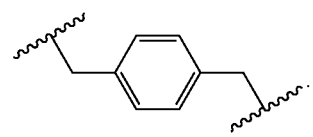

13. The method of claim 10, wherein said compound is administered per os to said patient.

14. The method of claim 10, wherein said compound is a compound of formula:

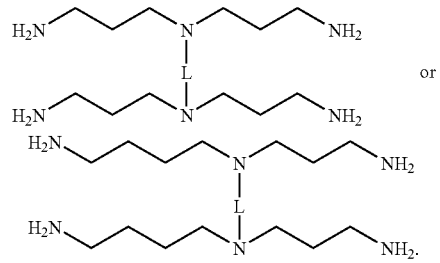

15. The method of claim 14, wherein L is

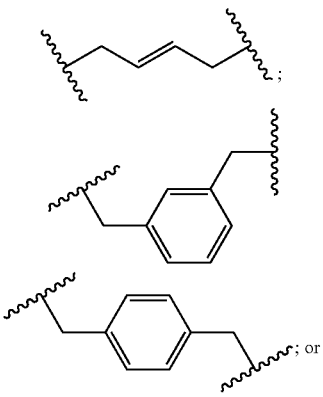

-continued

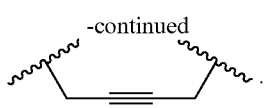

16. The method of claim 15, wherein L is

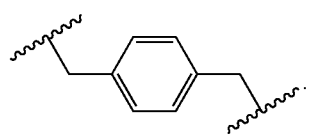

17. The method of claim 10, wherein the compound is administered in combination with an inhibitor of polyamine synthesis.

18. The method of claim 17, wherein the inhibitor of polyamine synthesis is α-difluoromethylornithine (DFMO).

19. The method of claim 10, wherein said disorder is carcinoma of the breast.

20. A method for treating cancer selected from leukemia and carcinoma of the breast comprising the step of administering to a patient a therapeutically effective amount of a compound of formula (I) or (II):

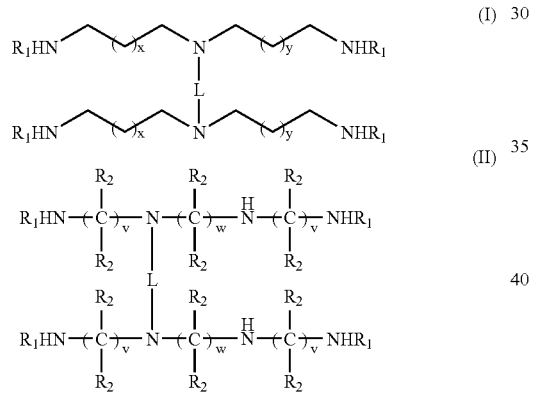

wherein
L is:

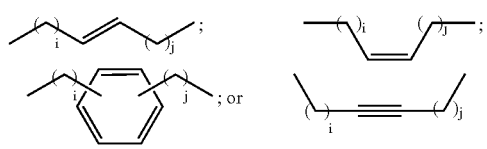

$R_1$=H, methyl, ethyl or propyl;
$R_2$=H or methyl;
$0<x<3$;
$0<y<3$;
$0<i<6$;
$0<j<6$;
$1\leq i+j\leq 7$;
$2<v<5$; and
$2<w<8$.

21. The method of claim 20, wherein L is

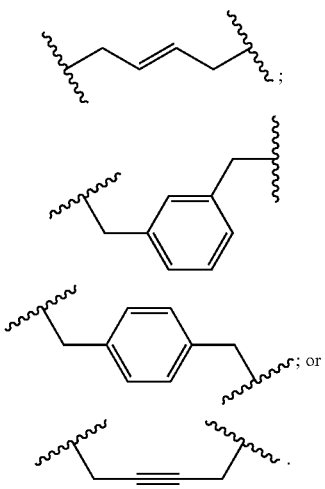

22. The method of claim 21, wherein L is

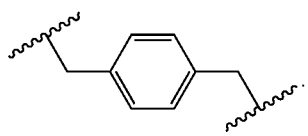

23. The method of claim 20, wherein said compound is administered per os to said patient.

24. The method of claim 20, wherein said compound is a compound of formula:

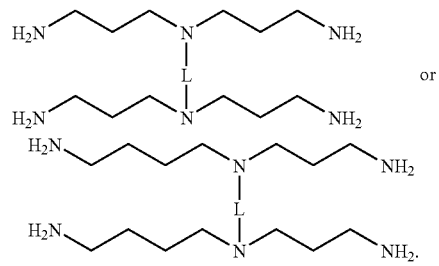

25. The method of claim 24, wherein L is

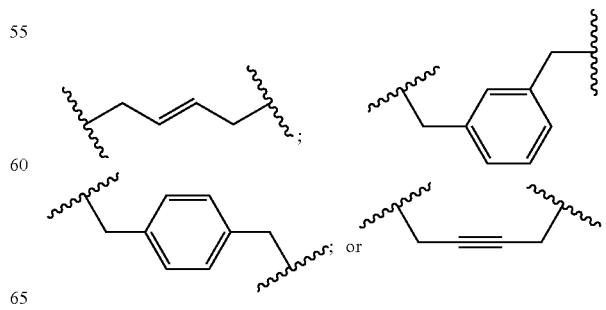

26. The method of claim 25, wherein L is
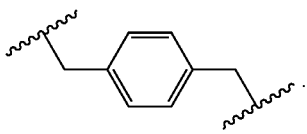
27. The method of claim 20, wherein the compound is administered in combination with an inhibitor of polyamine synthesis.
28. The method of claim 27, wherein the inhibitor of polyamine synthesis is α-difluoromethylornithine (DFMO).
29. The method of claim 20, wherein said cancer is carcinoma of the breast.
* * * * *